United States Patent
Krattiger et al.

(10) Patent No.: US 9,998,678 B2
(45) Date of Patent: Jun. 12, 2018

(54) CAMERA FOR ACQUIRING OPTICAL PROPERTIES AND SPATIAL STRUCTURE PROPERTIES

(71) Applicant: Karl Storz SE & Co. KG, Tuttlingen (DE)

(72) Inventors: Beat Krattiger, Beringen (CH); Martin Leonhard, Emmingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 211 days.

(21) Appl. No.: 14/244,325

(22) Filed: Apr. 3, 2014

(65) Prior Publication Data

US 2014/0300718 A1    Oct. 9, 2014

(30) Foreign Application Priority Data

Apr. 3, 2013  (DE) .......................... 10 2013 103 333

(51) Int. Cl.
*H04N 5/235* (2006.01)
*A61B 1/00* (2006.01)
(Continued)

(52) U.S. Cl.
CPC ....... *H04N 5/2354* (2013.01); *A61B 1/00009* (2013.01); *A61B 1/00193* (2013.01);
(Continued)

(58) Field of Classification Search
CPC ............ H04N 5/2354; H04N 13/0253; H04N 13/0257; G01S 7/4815; G01S 7/4816;
(Continued)

(56) References Cited

U.S. PATENT DOCUMENTS 7,956,988 B1 *  6/2011  Moran ............... G01B 11/2441
                                                    356/5.01
8,139,141 B2 *  3/2012  Bamji ...................... G01C 3/08
                                                    348/335
(Continued)

FOREIGN PATENT DOCUMENTS

DE    102007006351 A1    9/2007
DE    102006017003 A1    10/2007
(Continued)

*Primary Examiner* — Joseph Suh
(74) *Attorney, Agent, or Firm* — Whitmyer IP Group LLC

(57) ABSTRACT

A camera device acquires optical properties in two or more different wavelength ranges as well as spatial structure properties of an object. The device includes a beam splitter for splitting light coming from an object into the two or more different wavelength ranges. A first image sensor generates a first sensor signal related to a first predetermined wavelength range. A first signal processing device generates a first intensity image signal and a distance image signal using information about the temporal modulation of illumination light (M) and the first sensor signal. At least one second image sensor generates a second intensity image signal for a second predetermined wavelength range. A second signal processing device generates a color image signal from the first intensity image signal and the second intensity image signal.

21 Claims, 9 Drawing Sheets

(51) Int. Cl.

| | |
|---|---|
| *G01S 17/89* | (2006.01) |
| *G02B 23/24* | (2006.01) |
| *H04N 13/02* | (2006.01) |
| *A61B 1/04* | (2006.01) |
| *G01S 17/02* | (2006.01) |
| *G01S 17/36* | (2006.01) |
| *G01S 7/481* | (2006.01) |
| *G02B 27/10* | (2006.01) |
| *G01S 7/51* | (2006.01) |

(52) U.S. Cl.
CPC ............ *A61B 1/042* (2013.01); *G01S 7/4815* (2013.01); *G01S 7/4816* (2013.01); *G01S 17/023* (2013.01); *G01S 17/36* (2013.01); *G01S 17/89* (2013.01); *G02B 23/2415* (2013.01); *H04N 13/0253* (2013.01); *H04N 13/0257* (2013.01); *G01S 7/51* (2013.01); *G02B 27/1013* (2013.01)

(58) Field of Classification Search
CPC ........ G01S 17/023; G01S 17/36; G01S 17/89; G01S 7/51; G02B 23/2415; G02B 27/1013; A61B 1/00009; A61B 1/00193; A61B 1/042
See application file for complete search history.

(56) References Cited

U.S. PATENT DOCUMENTS

| | | | | |
|---|---|---|---|---|
| 2003/0209893 | A1* | 11/2003 | Breed | B60J 10/00 280/735 |
| 2004/0257677 | A1* | 12/2004 | Matsusaka | G02B 9/58 359/783 |
| 2005/0270528 | A1* | 12/2005 | Geshwind | G01J 3/02 356/330 |
| 2007/0040121 | A1* | 2/2007 | Kalayeh | G01C 11/025 250/342 |
| 2007/0158770 | A1 | 7/2007 | Kawahito | |
| 2007/0223887 | A1* | 9/2007 | Kanamori | G06T 3/4053 386/232 |
| 2007/0258319 | A1* | 11/2007 | Ronnekleiv | G01D 5/35383 367/20 |
| 2008/0029701 | A1* | 2/2008 | Onozawa | B60Q 1/0023 250/332 |
| 2008/0188716 | A1* | 8/2008 | Heckele | A61B 1/04 600/166 |
| 2009/0032679 | A1* | 2/2009 | Holladay | A61F 2/1618 250/201.2 |
| 2009/0092284 | A1* | 4/2009 | Breed | B60J 10/00 382/103 |
| 2010/0049055 | A1* | 2/2010 | Freudenberg | A61B 5/0059 600/475 |
| 2010/0053592 | A1* | 3/2010 | Yahav | G01S 7/486 356/4.01 |
| 2010/0108873 | A1* | 5/2010 | Schwertner | G01B 11/2504 250/252.1 |
| 2010/0128109 | A1* | 5/2010 | Banks | G01S 7/4816 348/46 |
| 2010/0258708 | A1* | 10/2010 | Meyers | G01S 17/36 250/208.1 |
| 2011/0051119 | A1* | 3/2011 | Min | G01S 7/491 356/5.1 |
| 2011/0101239 | A1* | 5/2011 | Woodhouse | G01S 7/4802 250/458.1 |
| 2011/0317005 | A1* | 12/2011 | Atkinson | G01S 17/023 348/135 |
| 2011/0317149 | A1* | 12/2011 | Shimbo | G01J 3/462 356/72 |
| 2012/0105823 | A1* | 5/2012 | Hardegger | G01S 17/023 356/5.01 |
| 2012/0120253 | A1* | 5/2012 | Corley | G01J 3/0262 348/180 |
| 2012/0157775 | A1* | 6/2012 | Yamaguchi | A61B 1/0638 600/180 |
| 2012/0307046 | A1* | 12/2012 | Lundberg | G01J 5/0022 348/135 |
| 2013/0016900 | A1* | 1/2013 | Kim | G06T 5/20 382/162 |
| 2013/0116977 | A1* | 5/2013 | Godbaz | G01S 17/89 702/189 |
| 2013/0175500 | A1* | 7/2013 | Cho | B82Y 20/00 257/21 |
| 2013/0178706 | A1* | 7/2013 | Shimada | A61B 1/00137 600/178 |
| 2014/0153596 | A1* | 6/2014 | Chuang | G02B 17/00 372/25 |
| 2014/0153816 | A1* | 6/2014 | Cohen | G06T 7/0075 382/154 |
| 2015/0001664 | A1* | 1/2015 | Van Der Tempel | H01L 27/14612 257/432 |

FOREIGN PATENT DOCUMENTS

| | | |
|---|---|---|
| DE | 102008018636 A1 | 10/2009 |
| DE | 102008018637 A1 | 10/2009 |
| EP | 2451150 A2 | 5/2012 |

* cited by examiner

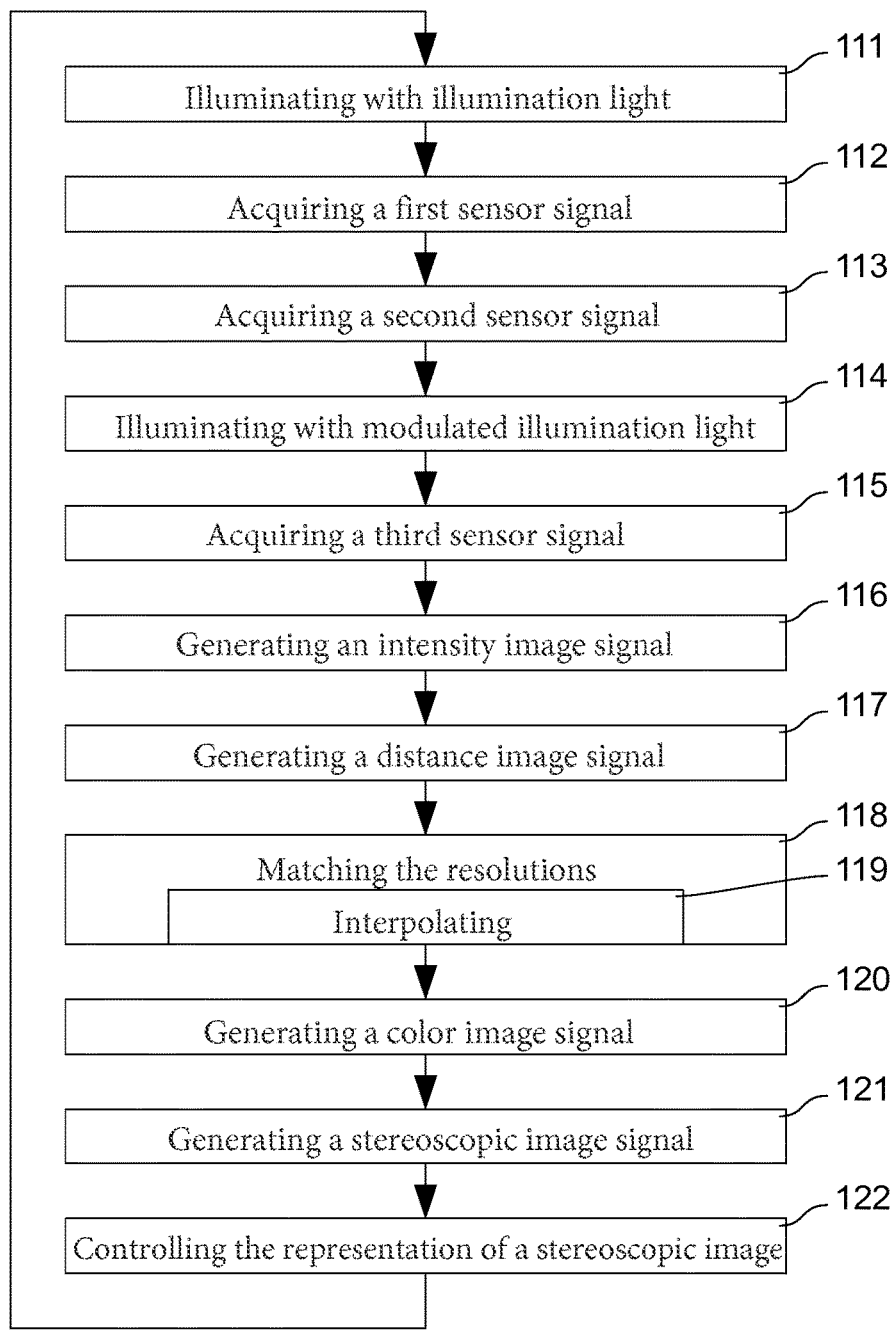

CAMERA FOR ACQUIRING OPTICAL PROPERTIES AND SPATIAL STRUCTURE PROPERTIES

FIELD OF THE INVENTION

The present invention is directed to a camera device, an endoscope or exoscope comprising a camera device, a method for producing a camera device and a method for acquiring optical properties and spatial structure properties of an object.

BACKGROUND OF THE INVENTION

Modern endoscopes, primarily if they comprise a video camera or are coupled to a video camera, are able to supply high-quality two-dimensional images from within a patient's body or from a cavity in a machine. However, a three-dimensional visual impression or a three-dimensional image is desirable for many applications. A three-dimensional image can enable a more accurate assessment of distances, lengths, areas, convex and concave curvatures and volumes and thus also support a more reliable diagnosis or a rapid, economic, safe and atraumatic intervention.

A stereoscopic endoscope, in which two images acquired from spaced-apart points are transmitted separately to the proximal end, in view of the required structural space and the tendency toward ever smaller shank cross sections, can be realized at best with extreme complexity and with other disadvantages being accepted. Therefore, a series of approaches exist for acquiring a high-quality two-dimensional image and in addition the distances between the observed surfaces and the distal end of the endoscope. Using the two-dimensional image and the distances, it is possible to calculate a stereoscopic image (with a respective partial image for the left eye and for the right eye of the observer) which imparts a three-dimensional impression to the observer. It is particularly advantageous that for this purpose, under certain circumstances, a conventional or only slightly modified endoscope can be used and a modification is necessary only on the camera device.

DE 10 2006 017 003 A1 (Jochen Penne, F A U Erlangen) describes an endoscope for depth data acquisition. A light source 102 emits infrared light modulated in accordance with modulation information (paragraphs [0046], [0051]). A photon mixing detector 108 receives light and generates a sensor signal representing the received light. The sensor signal is evaluated using the modulation information on the basis of the "time-of-flight" principle in order to calculate depth data from the time of flight of the received light signal (paragraphs [0018], [0030], [0042], [0047], [0048], [0049]). Besides a matrix of depth data or distance values, it is possible to generate a matrix of intensity information or intensity values from the sensor signal (paragraph [0018]). A further light source 202 for generating a daylight spectrum and a further sensor 302 can be provided for obtaining image data (paragraphs [0023], [0054], [0062]). Alternatively, the light source generates light in the visible spectrum range and an observer perceives the scene in this light (paragraph [0060]).

DE 10 2007 006 351 A1 (Frederic Sarrat, Logitech) describes an image acquisition. Light is split by means of a splitter and guided partly to a first sensor for acquiring information in two dimensions and partly to a second sensor for acquiring information in a third dimension (paragraphs [0011], [0012], [0036], [0040], [0041], [0046]). Furthermore, sensors are described which comprise, besides pixels for red (R), green (G) and blue light (B), infrared-sensitive pixels (D) for distance measurement (FIGS. 3A, 3B, 3C, paragraphs [0034], [0035]).

DE 10 2008 018 636 A1 (Beat Krattiger, Karl Storz) describes an endoscopic 3D data acquisition. By means of a beam splitter, radiation returning from an object is imaged onto one of a plurality of image sensors (paragraph [0018]). One sensor is phase-sensitive. If image sensors having different sensor sizes are used, a matching optical unit is arranged between the beam splitter and at least one image sensor (paragraph [0023]). A stereoscopic image is synthesized from a 2D image of the observed region and distance information (paragraphs [0036], [0037]).

DE 10 2008 018 637 A1 (Beat Krattiger, Karl Storz) describes a fluorescence imaging with a (temporally) modulated fluorescence excitation radiation (paragraphs [0011], [0012]). Fluorescence radiation is imaged onto a phase-sensitively drivable solid-state sensor (paragraphs [0019], [0020]). By means of a beam splitter, radiation received (from the illuminated object) is guided onto further sensors (paragraphs [0031], [0032], [0033]). In the case of sensors of different formats, a matching optical unit is provided (paragraph [0035]).

SUMMARY OF THE INVENTION

The present invention addresses the problem of providing an improved camera device, an improved endoscope or exoscope, an improved method for producing a camera device and an improved method for acquiring optical properties and spatial structure properties of an object.

This problem is solved by the subjects of the independent claims.

Developments are specified in the dependent claims.

Exemplary embodiments of the present invention are based on the concept of acquiring, by means of a ToF image sensor (ToF=Time of Flight), in particular by means of a phase-sensitive detector or by means of some other distance image sensor, not just a distance image but at the same time an intensity image in a color channel, which is combined with intensity images in further color channels to form a color image. An intensity image or an intensity image signal denotes an image or an image signal which comprises or specifies, for a (generally rectangular) raster of image points or pixels, a respective intensity value or brightness value in a color channel (for example red, green or blue). In general, a respective intensity image in the red, green and blue wavelength ranges or color channels are combined to form a color image. A color image contains, for each pixel, for example, a respective intensity value or brightness value in relation to each color channel. A distance image or a distance image signal denotes an image or an image signal which comprises, for each pixel, a distance between the surface element projected onto the pixel and the distal end of an endoscope or the lens of a camera.

The present invention is also based on the insight that many ToF sensors or other distance image sensors that actually operate or are operated in the infrared wavelength range have an intrinsic sensitivity in the red spectral range as well. These sensors can therefore be used simultaneously for acquiring an intensity image in the red spectral or wavelength range or in the red color channel. Therefore, acquiring a color image in three color channels (in particular blue, green and red) and a distance image does not necessitate four image sensors (one respectively for blue, green, red and distance). Rather, three image sensors suffice if both a distance image signal and an intensity image signal in relation to one of the color channels are generated by means of the distance sensor.

A camera device for acquiring optical properties in a plurality of different wavelength ranges and spatial structure properties of an object comprises a beam splitter for splitting light coming from an object into the plurality of different wavelength ranges; a first image sensor for generating a sensor signal related to a predetermined wavelength range, wherein the first image sensor, on the basis of a temporally modulatable sensitivity, is designed for acquiring a distance between an object and the camera device from a time of flight of light; a first signal processing device for generating a first intensity image signal and a distance image signal using information about the temporal modulation of illumination light and the first sensor signal, wherein the distance image signal represents spatial structure properties of the object; at least one second image sensor for generating a second intensity image signal for a second predetermined wavelength range; and a second signal processing device for generating a color image signal from the first intensity image signal and the second intensity image signal, wherein the color image signal represents optical properties of the object.

The camera device can be a camera comprising all devices and features mentioned here in a single unit, in particular within a single housing. Alternatively, the camera device can comprise a plurality of units connected to one another via electrical, optical or other signal lines. In particular, the camera device comprises a camera with the beam splitter and the image sensors, wherein the stated and further signal processing devices can be arranged in each case in the camera or in a further unit. The camera device is in particular produced according to one of the methods described below and/or designed for performing one of the methods described below for acquiring optical properties and spatial structure properties of an object. The camera device can partly or completely be integrated into an endoscope or into an exoscope or be designed for combination with an endoscope or with an exoscope.

The camera device is designed in particular for simultaneously or substantially simultaneously acquiring optical properties and spatial structure properties of an object. Optical properties and spatial structure properties of an object are also acquired substantially simultaneously if optical properties and spatial structure properties are acquired alternately (in particular with one of the customary image repetition frequencies in the range of 25 images per second to 100 images per second).

Optical properties in a plurality of different wavelength ranges of an object are in particular the degree of reflectance, the degree of reflection or fluorescence properties in the plurality of different wavelength ranges of the object.

Spatial structure properties of the object are, in particular, distances between surface regions of the object that are imaged onto the pixels of the first image sensor and the first image sensor, measured in each case along the optical path between object and image sensor. The path lengths along the optical path within the camera and, if appropriate, within an endoscope are constant. Therefore, distances between the object or its surface regions and the first image sensor and distances between the object or its surface regions and the front lens element of the camera device or the light entrance window of an endoscope that is optically coupled to the camera device differ merely in a predetermined summand. Therefore, the reference point or reference plane to which the distances are related will no longer be expressly mentioned hereinafter.

The camera device is designed for the spatially resolved acquisition of the optical properties and the spatial structure property. In particular, the camera device is designed for generating a multicolored image of the object in the plurality of different wavelength ranges or color channels (for example red, green, blue) and for generating a distance image. The multicolored image contains, for each of a plurality of pixels (in particular arranged in a rectangular raster), a respective intensity value or brightness value for each color channel or for each wavelength range. The distance image comprises a distance value for each of a plurality of pixels or pixel groups (in particular arranged in a rectangular raster). In this case, the resolution of the distance image can be lower than the resolution of the multicolored image.

The beam splitter can be any optical element which is suitable for splitting incident light into different wavelengths or wavelength ranges. It comprises in particular one or a plurality of prisms. Planar or curved dichroically (i.e. wavelength-dependently) reflective layers can be provided on the surfaces of said prisms or within the latter. The first image sensor, the second image sensor and optionally a third image sensor and, if appropriate, further image sensors are respectively assigned to one of the plurality of different wavelength ranges. Alternatively, one image sensor, in particular the second image sensor, can be assigned to a plurality of wavelength ranges. By way of example, the second image sensor comprises an alternating arrangement of pixels which are assigned to two different wavelength ranges and for this purpose are provided with color filters of two different types.

The assignment of an image sensor to a wavelength range (or to a plurality of wavelength ranges) can arise from the arrangement of the image sensor at a specific location relative to the beam splitter, in particular at a specific light exit surface of a beam splitter prism, to which only light in the assigned wavelength range passes. Alternatively or additionally, an image sensor can in each case be sensitive exclusively or predominantly for light in the assigned wavelength range. Each image sensor can be a location-sensitive or spatially resolving semiconductor sensor (for example CMOS or CCD).

The first image sensor is in particular a phase-sensitive detector, e.g. a ToF sensor. The first image sensor can be designed for generating a first sensor signal, which is related exclusively to the first predetermined wavelength range (in particular to the red range within the wavelength range visible to the human eye). Alternatively, the first sensor signal can furthermore be related to a further wavelength range (for example in the near or medium infrared).

The first image sensor is suitable for acquiring distances in particular on the basis of a sensitivity that is modulatable temporally at high frequency (tens of MHz, hundreds of MHz or more). Upon illumination of the object with illumination light which is modulated with a high frequency, in particular, and modulation of the sensitivity of the first image sensor with the same frequency, a signal whose phase is dependent on the distance between the object (along the optical path) and the first image sensor arises at each pixel of the first image sensor.

The second image sensor is provided and designed in particular for generating a sensor signal comprising a second intensity image signal for the blue wavelength range. Furthermore, in particular a third image sensor is provided and designed for generating a sensor signal comprising a third intensity image signal for the green wavelength range.

Furthermore, it is possible to provide further image sensors for further color channels in the ultraviolet, infrared or visible wavelength range.

Alternatively, the second image sensor for generating a sensor signal can acquire a third intensity image signal for the green wavelength range besides the second intensity image signal for the blue wavelength range. In particular, the second image sensor is a Bayer sensor or some other image sensor having two (or more) groups of pixels with color filters in two (or more) different colors arranged upstream thereof.

The first signal processing device, the second signal processing device and further signal processing devices mentioned or not mentioned hereinafter can be designed in each case as discrete analog or in particular digital circuits, as parts of integrated circuits as an FPGA (field programmable gate array) having a predetermined configuration or as part of an FPGA, as a processor or computer having firmware and/or software, as firmware or software or part of firmware or software for a processor or computer or as a combination thereof.

The first signal processing device is designed in particular for generating a first intensity image signal, which contains no distance information. In this case, a brightness that decreases with increasing distance between an object and the camera device on account of decreasing illuminance is no distance information within the meaning of the present description.

The first signal processing device is in particular furthermore designed to generate the distance image signal using information about the phase of the image signal with regard to a periodic modulation of illumination light. The first signal processing device can be partly or completely integrated into the first image sensor.

The second signal processing device is designed in particular to generate the color image signal from the first intensity image signal generated by means of the first image sensor and the first signal processing device, the second intensity image signal from the second image sensor and a third intensity image signal from a third image sensor. Alternatively, both the second intensity image signal and the third intensity image signal (and optionally further intensity image signals) can originate from the second image sensor. In this case, the second image sensor is in particular a Bayer sensor having a checkered arrangement of color filters upstream of a corresponding arrangement of light-sensitive cells of the image sensor.

The intensity image signal originating from the first image sensor can be the sole intensity image signal which is used by the second signal processing device for generating the color image signal and which is related to a specific wavelength range (in particular to the red wavelength range). Alternatively, the second signal processing device can be designed to combine the first intensity image signal from the first image sensor with a further intensity image signal in the same or in an overlapping wavelength range. A combination of the intensity image signals related to identical or overlapping wavelength ranges from the first image sensor and from a further image sensor can enable a reduction of color noise, an improvement in the color rendering or an improved differentiation between malignant and benign tissue.

The double use of the first image sensor both for generating a distance image signal and for generating an intensity image signal in the first predetermined wavelength range can thus enable a reduction of the number of image sensors used overall and/or an improvement in the color rendering and/or support a differentiation of benign and malignant tissue.

In the case of a camera device such as is described here, the first wavelength range lies in particular at least partly within the wavelength range visible to the human eye.

Electromagnetic radiation having wavelengths in the range of approximately 380 nm to approximately 750 nm is visible to the human eye. The first wavelength range comprises in particular wavelengths perceived as red by the human eye (approximately 600 nm to 750 nm).

In the case of a camera device such as is described here, the first wavelength range lies in particular at least partly within the infrared wavelength range (wavelengths greater than 750 nm).

In the case of a camera device such as is described here, the second signal processing device is designed in particular to generate the color image signal without using the distance image signal.

The second signal processing device therefore does not generate for instance an image signal for an image in which distances are coded by colors, for example. Rather, the second signal processing device is designed to generate a color image signal which—apart from the image brightness that decreases with increasing distance of the object—contains no information about the distance and is generated without using information about distances.

A camera device such as is described here is produced in particular by the removal of an image sensor on the beam splitter and the replacement of the removed image sensor by the first image sensor.

The production of the camera device comprises further steps (not mentioned here) besides the steps of removal and replacement.

A camera device such as is described here in particular furthermore comprises a third signal processing device for generating a stereoscopic image signal.

The third signal processing device is designed in particular to receive and to use the color image signal and the distance image signal to generate the stereoscopic image signal. The stereoscopic image signal is designed for controlling a reproduction of two different images provided each for a respective eye of an observer. The third signal processing device generates the stereoscopic image signal in particular by a displacement of pixels of the color image signal depending on the assigned distances in directions that are opposite for both eyes.

In the case of a camera device such as is described here, the first image sensor and the second image sensor have in particular different resolutions, wherein the camera device furthermore comprises a signal processing device for matching a first resolution of the first intensity image signal and a second resolution of the second intensity image signal to one another.

Said further signal processing device can be partly or completely integrated with or identical to the first image sensor and/or the first signal processing device and/or the second signal processing device. The further signal processing device is in particular provided and designed to match the resolution of that intensity image signal having a lower resolution to the resolution of that intensity image signal having a higher resolution.

In many cases, image sensors suitable for acquiring distances on the basis of their sensitivity that is modulatable temporally at high frequency have a comparatively low or very low resolution. Therefore, for example, the first image sensor has in each case only a few hundred columns and rows of pixels. By contrast, the second image sensor and, if appropriate, the third image sensor have for example in each case a resolution of 1920×1080 pixels.

In the case of a camera device such as is described here, the further signal processing device is designed in particular to interpolate, for the purpose of matching different resolutions, the intensity image signal having the lower resolution for positions of pixels of the intensity image signal having the higher resolution.

In particular, the further signal processing device is designed to use, for the purpose of interpolation, information from the intensity image signal having the higher resolution.

In particular, the first intensity image signal (which is related in particular exclusively, predominantly or at least partly to the red wavelength range) originating from the first image sensor is interpolated for positions of pixels of the second intensity image signal (in particular related to the green wavelength range) originating from the second image sensor and, if appropriate, of the third intensity image signal (in particular related to the blue wavelength range) originating from the third image sensor. In particular information about edges and other structures contained in the second intensity image signal and, if appropriate, in the third intensity image signal is used during the interpolation. By way of example, intensity values or brightness values of the second intensity image signal and, if appropriate, of the third and further intensity image signals are approximated by splines or polynomials, the coefficients of which are then used for interpolating the first intensity image signal.

In the case of a camera device such as is described here, the first image sensor and the second image sensor have in particular different dimensions, wherein the camera device furthermore comprises a device for matching the sensor sizes to one another.

The device for matching the sensor sizes comprises in particular an arrangement of one or a plurality of lens elements between the beam splitter and the first image sensor and/or an arrangement of one or a plurality of lens elements between the beam splitter and the second image sensor in order to match to one another the solid angle ranges within which objects are imaged onto the first image sensor and/or onto the second image sensor. In the case of different ratios between width and height at the first image sensor and at the second image sensor, the device for matching the sensor sizes is designed for anamorphic imaging or is or comprises an anamorphic lens.

An endoscope or exoscope comprises a camera device such as is described here. The camera device can be connected to the endoscope or exoscope permanently or in such a manner that it cannot be separated nondestructively without the use of tools. In particular, the camera device can be provided at the proximal end or at the distal end of an endoscope. Alternatively, the endoscope or exoscope can be designed such that the camera device can be separated nondestructively without the use of a tool. An exoscope, in contrast to an endoscope, is not provided for being inserted into a cavity in a patient's body or in a machine. Instead, an exoscope is typically provided and designed for being arranged at a distance of some or a few decimeters or some or a few centimeters outside the body or the machine. An exoscope forms in particular an extracorporeal visualization device for surgical interventions.

A method for producing a camera device for acquiring optical properties in a plurality of different wavelength ranges and spatial structure properties of an object comprises providing a beam splitter for splitting light into a plurality of different wavelength ranges, wherein a respective light-sensitive image sensor is provided on the beam splitter for each of the plurality of different wavelength ranges; removing an image sensor from the beam splitter; and replacing the removed image sensor by a first image sensor, which, on the basis of temporally modulatable sensitivity, is designed for acquiring a distance between an object and the camera device from a time of flight of light, wherein a second image sensor remains at the beam splitter.

The method is designed in particular for producing a camera device such as is described here. In this respect, reference is made to the above presentation of features, properties, functions and advantages of a camera device. The method is designed in particular for producing a camera device for carrying out a method for acquiring optical properties in a plurality of different wavelength ranges and spatial structure properties of an object as described below. In this respect, reference is made to the presentation of features, properties, effects and advantages of the method further below.

On the beam splitter, in particular on three light exit surfaces, a respective image sensor is provided, one each for the blue, the green and the red wavelength ranges. Alternatively, the beam splitter can have only two light exit surfaces and two image sensors. By way of example, one image sensor is assigned to the red wavelength range and one image sensor to the green and the blue wavelength ranges. The image sensor assigned to the green and the blue wavelength ranges can be designed to generate simultaneously or alternately intensity image signals (which can be interlaced in one another) in relation to the green and the blue wavelength ranges. Alternatively, the beam splitter can have four or more light exit surfaces each having an image sensor for a respective wavelength range from a corresponding number of different wavelength ranges.

The removed image sensor is assigned in particular to the wavelength range perceived as red by the human eye (approximately 600 nm to approximately 750 nm).

In particular beam splitters having three light exit surfaces and three image sensors are available in a great variety and in some instances at favorable prices, for example as high-quality video cameras or for high-quality video cameras. Removing one of the image sensors from the beam splitter and replacing it by an image sensor suitable for acquiring distances can constitute a particularly cost-effective way of producing a camera device having the desired properties.

In the case of a production method such as is described here, the first image sensor is sensitive in particular in the wavelength range which was assigned to the removed image sensor.

The wavelength range assigned to the removed image sensor is in particular the wavelength range perceived as red by the human eye. Alternatively, the wavelength range assigned to the removed image sensor can be for example a wavelength range perceived as blue and green by the human eye. Both the removed image sensor and the first image sensor replacing it can each additionally be sensitive in further wavelength ranges, for example in the infrared.

A production method such as is described here involves in particular furthermore providing a first signal processing device for receiving a first sensor signal from the first image sensor and for generating a first intensity image signal and a distance image signal using the first sensor signal of the first image sensor.

Providing comprises in particular coupling or effectively connecting the first signal processing device to the first image sensor by means of electrical, optical or other signal lines for transmitting analog or digital signals from the first image sensor to the first signal processing device. The first signal processing device can be partly or completely integrated with the first image sensor. In this case, the step of replacing the removed image sensor by the first image sensor comprises providing the first signal processing device.

The first signal processing device is designed in particular (as already described above for the camera device) for generating the distance image signal using information about a temporal modulation of the illumination light.

A production method such as is described here involves furthermore in particular providing a second signal processing device for receiving the first intensity image signal, for receiving a second intensity image signal for a second predetermined wavelength range from the second image sensor and for generating a color image signal using the first intensity image signal and the second intensity image signal.

The second signal processing device is in particular furthermore designed for receiving a third sensor signal, which comprises a third intensity image signal for a third predetermined wavelength range, from a third image sensor on the beam splitter and for generating a color image signal also using the third intensity image signal. Alternatively, the second signal processing device is designed to receive from the second image sensor a sensor signal comprising the second intensity image signal and a third intensity image signal for a third predetermined wavelength range and optionally a fourth or further intensity image signal(s) for a fourth or further predetermined wavelength range(s). Furthermore, the second signal processing device can be designed for receiving further sensor signals comprising further intensity image signals, and for generating the color image also using said further intensity image signals.

Providing the second signal processing device comprises in particular coupling or effectively connecting the second signal processing device to the first signal processing device, to the second image sensor and, if appropriate, to further image sensors by means of electrical, optical or other signal lines for transmitting analog or digital signals.

In a production method such as is described here, the second signal processing device is designed in particular to generate the color image signal without using the distance image signal.

In a production method such as is described here, the second signal processing device is coupled to the first signal processing device in particular such that the second signal processing device does not receive the distance image signal.

A production method such as is described here involves in particular furthermore providing a third signal processing device for receiving the color image signal, for receiving the distance image signal and for generating a stereoscopic image signal using the color image signal and the distance image signal.

Providing the third signal processing device comprises in particular coupling or effectively connecting the third signal processing device to the first signal processing device and to the second signal processing device by means of electrical, optical or other signal lines for transmitting analog or digital signals.

A production method such as is described here involves furthermore in particular providing a further signal processing device for matching a first resolution of the first intensity image signal and a second resolution of the second intensity image signal to one another.

Providing the further signal processing device comprises in particular coupling or effectively connecting the further signal processing device to the first signal processing device, to the second signal processing device and optionally to the second image sensor and if appropriate and optionally to one or a plurality of further image sensors by means of electrical, optical or other signal lines for transmitting analog or digital signals.

A production method such as is described here involves in particular providing a further signal processing device for matching resolutions, which is designed to interpolate an intensity image signal having a lower resolution for positions of pixels of an intensity image signal having a higher resolution.

The further signal processing device provided is designed in particular to use, for the purpose of interpolation, information from the intensity image signal having the higher resolution.

Each of the steps of providing the first signal processing device, providing the second signal processing device, providing the third signal processing device and providing the further signal processing device can be performed partly or completely simultaneously with providing the first image sensor or with the step of replacing the removed image sensor by the first image sensor at the same time. In particular, the first signal processing device, the second signal processing device, the third signal processing device and the further signal processing device are in each case partly or completely integrated with the first image sensor in one component.

A method for acquiring optical properties in a plurality of different wavelength ranges and spatial structure properties of an object comprises illuminating the object with illumination light that is temporally modulated in a predetermined manner; acquiring a first sensor signal, which is related to a first predetermined wavelength range, by means of a first image sensor having temporally modulated sensitivity; generating a first intensity image signal using the first sensor signal; generating a distance image signal using information about the temporal modulation of the illumination light and the first sensor signal; acquiring a second intensity image signal, which is related to a second predetermined wavelength range, by means of a second image sensor; and generating a color image signal using the first intensity image signal and the second intensity image signal, wherein the color image signal represents optical properties of the object and the distance image signal represents spatial structure properties of the object.

The method is designed in particular for endoscopically and in particular for simultaneously or substantially simultaneously acquiring optical properties in a plurality of different wavelength ranges and spatial structure properties of an object. The method can be performed in particular by means of a camera device such as is described here, or by means of a camera device produced by a production method such as is described here. In this respect, reference is made to the presentation of features, properties, functions, effects and advantages of camera devices and production methods above.

The illumination light can be completely modulated or have exclusively modulated spectral components. Alternatively, the illumination light can have temporally modulated and unmodulated components. In particular, that wavelength range or part of that wavelength range for which the first image sensor is sensitive is temporally modulated. The illumination light can be unmodulated in a wavelength range in which the first image sensor is not sensitive. In so far as an impairment of the signal-to-noise ratio is accepted, components of the illumination light for which the first image sensor is sensitive can also be unmodulated. By way of example, if the first image sensor only acquires light in the red wavelength range, the illumination light can comprise temporally modulated white light or simultaneously unmodulated blue and green light and temporally modulated red light or alternately unmodulated white light and temporally modulated red light. In the last-mentioned case, the distance image signal can be generated in particular in the time intervals in which the illumination light only comprises temporally modulated red light. Alternatively, the illumination light can simultaneously comprise temporally unmodulated white light and temporally modulated red light, as a result of which the signal-to-noise ratio can be impaired.

The distance image signal is generated in particular using information about the phase and/or the frequency of the periodic modulation.

In addition, a third intensity image signal, which is related to a third predetermined wavelength range, can be acquired by means of the second image sensor or by means of a third image sensor, wherein the color image signal is generated using the third intensity image signal as well.

In the case of a method for acquiring optical properties and spatial structure properties, the color image signal is generated in particular without using the distance image signal.

In the case of a method for acquiring optical properties and spatial structure properties such as is described here, a stereoscopic image signal is furthermore generated in particular using the color image signal and the distance image signal.

By means of the stereoscopic image signal, a representation of a stereoscopic image can be controlled, for example by the representation of two different-colored images of an anaglyphic image, by means of a shutter method, a polarization system or a lens element grid (autostereoscopy).

A method for acquiring optical properties and spatial structure properties such as is described here and wherein the resolutions of the first intensity image signal and of the second intensity image signal differ from one another involves furthermore in particular matching the resolutions to one another.

The resolutions are matched in particular by the lower resolution being matched to the higher resolution.

In the case of a method for acquiring optical properties and spatial structure properties such as is described here, matching the resolutions comprises in particular interpolating the intensity image signal having the lower resolution for positions of pixels of the image signal having the higher resolution.

In the case of a method for acquiring optical properties and spatial structure properties such as is described here, matching the resolutions comprises interpolating the intensity image signal having the lower resolution for positions of pixels of the image signal having the higher resolution using information from the image signal having the higher resolution.

BRIEF DESCRIPTION OF THE DRAWINGS

Embodiments are explained in greater detail below with reference to the accompanying figures, in which:

FIG. 16 shows a schematic flowchart of a method for acquiring optical properties and spatial structure properties.

DETAILED DESCRIPTION OF THE INVENTION

Figure 1:
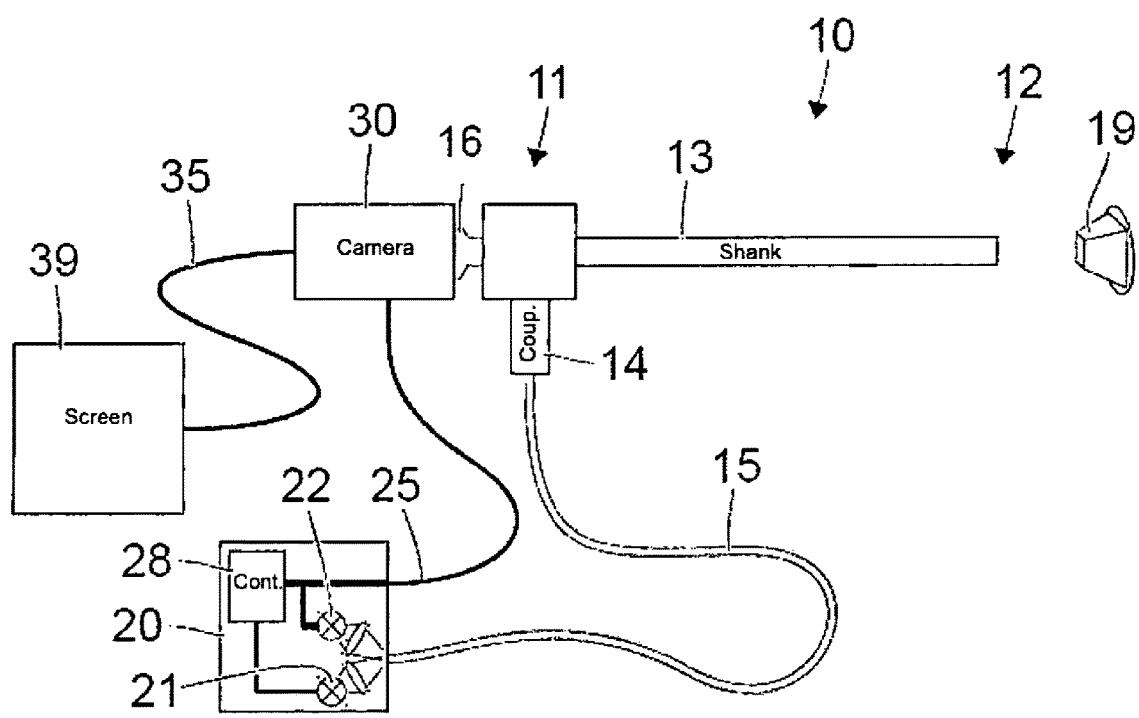
FIG. 1 shows a schematic illustration of an endoscope comprising a camera device.

FIG. 1 shows a schematic illustration of an endoscope 10 comprising a light source device 20 and a camera 30. The endoscope 10 comprises a proximal end 11 and a distal end 12. A rigid and straight shank 13 extends from the proximal end 11 as far as the distal end 12 of the endoscope 10. In a departure from the illustration in FIG. 1, the shank 13 can be embodied as curved and/or partly or completely flexible. A coupling 14 for an optical-fiber cable 15 for illumination light and an eyepiece 16 are provided at the proximal end 11 of the endoscope 10.

The light source device 20 comprises a first light source 21 and a second light source 22, the light from which is coupled into the optical-fiber cable 15, indicated in FIG. 1 by two lens elements without reference signs. Furthermore, the light source device 20 comprises a controller 28 for controlling the first light source 21 and the second light source 22.

A camera 30 is mechanically and optically coupled to the eyepiece 16 of the endoscope 10. Alternatively, in a departure from the illustration in FIG. 1, the camera 30 can be partly or completely integrated into the endoscope 10. The camera 30 is coupled via a signal cable 25 to the light source device 20, in particular to the controller 28 of the light source device 20. Furthermore, the camera 30 is coupled via a further signal cable 35 to a screen 39.

The light source device 20 is designed to generate illumination light that is guided by means of the optical-fiber cable 15 to the proximal end 11 of the endoscope 10 and by means of one or a plurality of optical waveguides in the shank 13 to the distal end 12 of the endoscope 10. At the distal end 12 of the endoscope 10, the illumination light generated by the light source device 20 emerges and is incident on an article or an object 19.

Illumination light returned or reflected from the object 19 and light emitted by the object 19 (for example by fluorescence) are partly coupled into the endoscope 10 at the distal end 12. If the camera 30 is arranged at the proximal end 11 of the endoscope 10, as illustrated in FIG. 1, the light emerging from the object 19 is transmitted for example by means of a plurality of rod lens elements arranged one behind another in the rigid shank 13 or, particularly in the case of an elastic or plastic flexibility of the shank 13, by means of an ordered bundle of optical fibers from the distal end 12 to the proximal end 11 of the endoscope 10.

In the camera 30, the light emerging from the object 19 is guided onto a plurality of light-sensitive image sensors. In this case, images of the object 19 in a plurality of different wavelength ranges arise on the image sensors. The image sensors generate sensor signals that are processed by signal processing devices in order to generate a stereoscopic image signal. The stereoscopic image signal is transmitted by means of the signal cable 35 to the screen 39, where it controls the representations of two images, one each of which is respectively provided for the left eye and the right eye of the observer.

The two images are represented for example alternately on the screen 39, the observer wearing shutter spectacles that shade the left eye and the right eye of the observer synchronously with the alternate representation of the two images. Alternatively, the two images are represented on the screen 39 in light having different polarizations, the observer bearing two different polarization filters in front of said observer's eyes. Alternatively, the two images can be represented on the screen 39 in different colors, the observer wearing two different-colored filters in front of said observer's eyes. Alternatively, the screen 39 has an arrangement of lens elements or diaphragms, such that the two eyes of the observer see partly or completely disjoint subsets of pixels. Alternatively, the observer can wear two screens, one in front of each eye. In this case, in a departure from the illustration in FIG. 1, no screen 39 is required. Instead, the stereoscopic image signal is transmitted by means of the signal cable 35 or by means of a radio link to a device similar to spectacles and comprising the two screens on the observer.

The light sources 21, 22 of the light source device 20 are designed to generate light having two different emission spectra. In particular, the first light source 21 is designed for generating light having a first emission spectrum and the second light source 22 is designed for generating light having a second emission spectrum. The two emission spectra of the light sources 21, 22 can partly or completely overlap or be largely or completely disjoint.

The controller 28 of the light source device 20 is designed to generate a high-frequency modulation signal. The high-frequency modulation signal firstly controls the second light source 22, in order to correspondingly modulate the emission of the second light source 22, and secondly is transmitted by means of the signal cable 25 to the camera 30. Alternatively, in a departure from the illustration in FIG. 1, only a signal that indicates the phase of the modulation of the emission of the second light source 22 or is in a predetermined phase relation with the modulation is transmitted to the camera.

Figure 2:
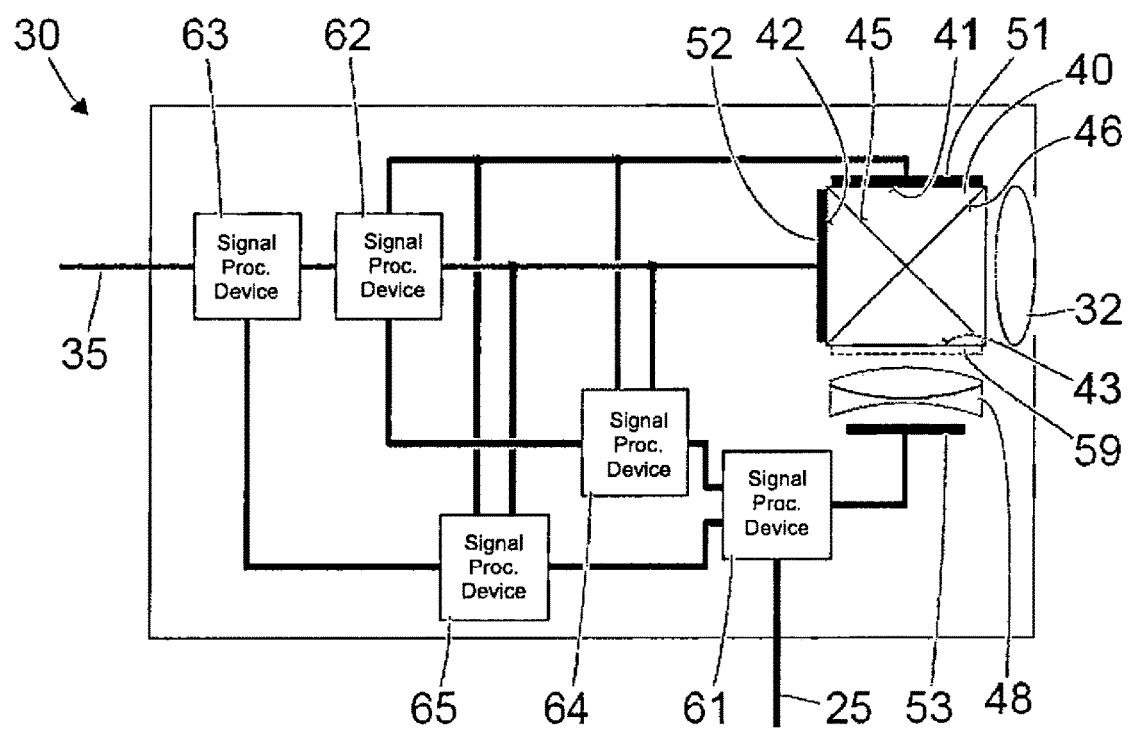
FIG. 2 shows a schematic illustration of a camera device.

FIG. 2 shows a schematic illustration of the camera 30 from FIG. 1. The camera 30 comprises an imaging device 32, in particular a lens, a lens-element or mirror system, for optically coupling the camera to the eyepiece 16 of the endoscope 10 (cf. FIG. 1). Devices for mechanically coupling the camera 30 to the endoscope 10 are not illustrated in FIG. 2.

The camera 30 furthermore comprises a beam splitter in the form of a prism 40 having light exit surfaces 41, 42, 43 and dichroically reflective layers 45, 46 in the prism 40. The dichroically reflective layers 45, 46 in the prism 40 are designed such that light entering into the prism 40 through the imaging device 32 leaves at one of the three light exit surfaces 41, 42, 43 depending on the wavelength of said light. In particular, light having medium wavelengths passes to the second light exit surface 42, the first dichroically reflective layer 45 directs light having short wavelengths to the first light exit surface 41, and the second dichroically reflective layer 46 directs light having long wavelengths to the third light exit surface 43.

It is assumed hereinafter by way of example that the first dichroically reflective layer 45 reflects light in the wavelength range perceived as blue by the human eye to the first light exit surface 41, the second dichroically reflective layer 46 reflects light in the wavelength range perceived as red by the human eye to the third light exit surface 43 and light in the wavelength range perceived as green by the human eye passes to the second light exit surface 42. In a departure from this example used below, however, provision can be made of other reflective properties of the dichroically reflective layers 45, 46 and correspondingly an assignment of the light exit surfaces 41, 42, 43 of the prism 40 to other wavelength ranges.

An image sensor 51 assigned to the blue wavelength range is arranged at the first light exit surface 41. An image sensor 52 assigned to the green wavelength range is arranged at the second light exit surface 42. A sensor 59 assigned to the red wavelength range may have been arranged at the third light exit surface 43 originally or before the state illustrated in FIG. 2. Said image sensor 59 is indicated merely by a dashed line in FIG. 2 since it has been removed and replaced by a matching optical unit 48, for example an anamorphic lens, and an image sensor 53 assigned to the red and infrared wavelength range. Alternatively, the configuration illustrated here with reference to FIG. 2 can be the original configuration produced.

In the case of the example illustrated in FIG. 2, the image sensor 51 assigned to the blue wavelength range and the image sensor 52 assigned to the green wavelength range, on the one hand, and the image sensor 53 assigned to the red wavelength range, on the other hand, have different sizes, i.e. different widths and/or different heights. The anamorphic lens 48 is provided and designed to acquire an image by means of the image sensor 53 assigned to the red wavelength range, the width and height of which image corresponds as exactly as possible to the images acquired by the other two image sensors 51, 52.

If the image sensor 53 assigned to the red wavelength range has the same format as the other two image sensors, a matching optical unit, in particular an anamorphic lens 48, can be omitted. In this case, in a departure from the illustration in FIG. 2, the image sensor 53 assigned to the red wavelength range is arranged directly at the third light exit surface 43 of the prism 40 (in particular is cemented to the latter) in particular in the same way as the other image sensors 51, 52 are arranged at the other two light exit surfaces 41, 42.

Independently of possibly different dimensions, it is assumed hereinafter that the image sensor 53 assigned to the red wavelength range also has a different resolution or a different, in particular smaller, number of pixels.

The image sensor 53 assigned to the red and infrared wavelength range is in particular a phase-sensitive ToF image sensor that is suitable for acquiring distances from times of flight of light signals on the basis of a temporally high-frequency modulatable sensitivity. In one widely used design of a ToF image sensor, the charge carriers generated in a photosensitive element (for example a photodiode) of a pixel are collected alternately at high frequency by two storage elements (in particular capacitors). In the case of a high-frequency modulated illumination of the acquired object, the ratio of the charges collected in the storage elements, in the same way as the ratio of the voltages present at the storage elements, is a simple function of the phase difference between the modulation of the light incident on the photosensitive element and the high-frequency alternate switching of the storage elements. This phase difference is in turn a simple function of the sum of the time of flight of the illumination light to the object and the time of flight of the reflected or returned light from the object to the photosensitive element and thus a function of the distance. From the ratio of the voltages at the two storage elements of a pixel, it is therefore possible to deduce the distance between that surface region of an acquired object which is imaged onto the pixel and the image sensor.

On account of the significantly more complex construction of the individual pixel and in particular also on account of the required high capacitances of the storage elements assigned to each pixel, the individual storage element of a ToF image sensor is generally significantly larger than a pixel of some other image sensor. Correspondingly, the resolution or the number of pixels of a ToF image sensor is generally significantly lower than the resolution of some other image sensor. In many cases, ToF image sensors are not or not only sensitive in the red wavelength range, but instead or in addition in the infrared wavelength range and are operated in the infrared wavelength range.

It is assumed hereinafter that the image sensor 53 provided for the red wavelength range is a ToF image sensor that is sensitive in the red and in the infrared wavelength range and has a significantly lower resolution than the image sensors 51, 52 assigned to the blue and to the green wavelength range.

The camera 30 comprises a first signal processing device 61 having a signal input coupled to the signal output of the ToF image sensor 53 in order to receive a sensor signal from the latter. The first signal processing device 61 is designed to obtain a signal from the light source device 20 (cf. FIG. 1) via the signal cable 25, said signal indicating at least the phase of the modulation of the illumination light generated by the light source device 20. The first signal processing device 61 is designed to generate an intensity image signal and a distance image signal using the sensor signal received from the ToF image sensor 53 and the information about the phase of the modulation of the illumination light.

The intensity image signal generated by the first signal processing device 61 indicates, for each pixel of the ToF image sensor 53, the intensity or brightness integrated or summed over a plurality of periods of the modulation. The intensity image signal generated by the first signal processing device 61, on account of the properties of the prism 40 and the arrangement of the ToF image sensor 53 at the prism 40, is related to the red and infrared wavelength range emerging at the third light exit surface 43 of the prism 40.

The distance image signal generated by the first signal processing device 61 indicates, for each pixel of the ToF image sensor 53, the distance—determined for example in the manner outlined above—between that surface region of the object 19 (cf. FIG. 1) which is imaged onto the pixel and the camera 30 or the distal end 12 of the endoscope 10.

The first signal processing device 61 can—in a departure from the schematic illustration in FIG. 2—be integrated with the ToF image sensor 53. In the case of the example illustrated, the first signal processing device 61 is designed to output the intensity image signal, on the one hand, and the distance image signal, on the other hand, to two different downstream devices (and in particular via two separate outputs).

The camera 30 comprises a second signal processing device 62, the signal inputs of which are coupled to the signal output of the image sensor 51 assigned to the blue wavelength range, to the signal output of the image sensor 52 assigned to the green wavelength range and (indirectly via a signal processing devices 64 described below) to a signal output of the first signal processing device 61. The second signal processing device 62 receives from the image sensors 51, 52 and from the first signal processing device 61 three intensity image signals, of which respectively one is related to the blue wavelength range, one is related to the green wavelength range and one is related to the red and infrared wavelength range. The second signal processing device 62 is designed to generate a color image signal from the intensity image signals. Said color image signal contains no information about distances—apart from the brightness that decreases with increasing distance on account of decreasing illuminance and apart from the sharpness that is different on account of different distances. In particular, the distance image signal generated by the first signal processing device 61 does not influence the generation of the color image signal by the second signal processing device 62.

The camera 30 furthermore comprises a third signal processing device 63 having signal inputs coupled to a signal output of the second signal processing device 62 and (indirectly via a signal processing device 65 described below) to the first signal processing device 61 in order to receive the color image signal and the distance image signal from them. The third signal processing device 63 is designed to generate a stereoscopic image signal using the color image signal received from the second signal processing device and the distance image signal received from the first signal processing device, said stereoscopic image signal being transmitted to the screen 39 (cf. FIG. 1) in particular by means of the signal cable 35.

The third signal processing device 63 is designed to generate two slightly different images each provided respectively for one eye of a human observer, in which images pixels or image points are displaced in opposite directions by displacements dependent on the associated distance. When two images generated by said stereoscopic image signal are observed each respectively by one eye, the human observer is given a three-dimensional image impression that simplifies the assessment of distances, lengths, areas and volumes.

Furthermore, the third signal processing device 63 can be designed, using the color image signal and the distance image signal, to calculate lengths, areas and volumes of acquired objects and to store them in one or more tables or to output them alphanumerically visually or acoustically.

The camera 30 furthermore comprises a fourth signal processing device 64 between the first signal processing device 61 and the second signal processing device 62. The fourth signal processing device 64 is provided and designed to receive the intensity image signal generated by the first signal processing device 61 and to forward it in modified form to the second signal processing device 62.

The fourth signal processing device 64 is designed to match the resolution, i.e. the number of columns and lines of the pixels, of the intensity image signal generated by the first signal processing device 61 in the red range to the resolutions of the intensity image signals which the second signal processing device 62 receives from the image sensors 51, 52 assigned to the blue and to the green wavelength range. In particular, the fourth signal processing device 64 is designed to interpolate the intensity image signal generated by the first signal processing device 61 for positions of pixels of the intensity image signals which originate from the image sensors 51, 52 assigned to the blue and to the green wavelength range.

For this purpose, the fourth signal processing device 64 in particular also receives the intensity image signals originating from the image sensors 51, 52 assigned to the blue and to the green wavelength range. The fourth signal processing device 64 is designed, in particular, to identify edges and other structures in the intensity image signals assigned to the blue and to the green wavelength range and to transfer them to the intensity image signal assigned to the red wavelength range. In particular, splines or polynomials or other functions are matched or fitted to the intensity image signals assigned to the blue and to the green wavelength range and the coefficients or parameters thus obtained are used partly or completely in the interpolation of the intensity image signal assigned to the red wavelength range.

Furthermore, the camera 30 comprises a fifth signal processing device 65 between the first signal processing device 61 and the third signal processing device 63. The fifth signal processing device 65 is designed to receive the distance image signal generated by the first signal processing device 61 and to match its resolution to the intensity image signals assigned to the blue and to the green wavelength range. For this purpose, the fifth signal processing device 65 is designed in particular similarly or identically to the fourth signal processing device 64.

The signal processing devices 61, 62, 63, 64 can be designed in the form of discrete or integrated but separate circuits, in particular electronic circuits. Alternatively, the signal processing devices 61, 62, 63, 64, 65 can be integrated in each case partly or completely with one of the image sensors 51, 52, 53, in particular with the ToF image sensor 53, or among one another. In particular, the first signal processing device 61 is integrated with the ToF image sensor 53. The signal processing devices 61, 62, 63, 64, 65 can be designed in each case partly or completely in the form of one or more FPGAs having a predetermined configuration and in each case partly or completely in the form of software or firmware for one or more processors or a computer.

All the signal processing devices 61, 62, 63, 64, 65 can be arranged—as indicated in FIG. 2—together with the beam splitter and the image sensors 51, 52, 53 in a common housing and thus as part of a single camera unit. Alternatively, said signal processing devices 61, 62, 63, 64, 65 can be arranged partly or completely in one or more separate units, for example in the form of a computer and/or in a manner integrated with the screen 39 (cf. FIG. 1). Independently of their spatial arrangement, in particular independently of whether all the signal processing devices 61, 62, 63, 64, 65 are arranged together with the beam splitter 40 and the image sensors 51, 52, 53 in a common housing or in a plurality of separate units, all the signal processing devices 61, 62, 63, 64, 65 illustrated in FIG. 2, the beam splitter 40 and the image sensors 51, 52, 53 are parts of a camera device within the meaning of the present description.

Figure 3:
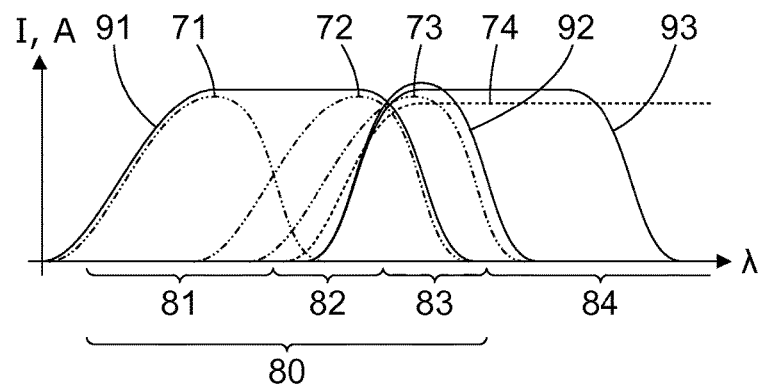
FIG. 3 shows a schematic illustration of wavelength ranges, intensities and spectral sensitivities.

FIG. 3 shows a schematic illustration of wavelength ranges, spectral sensitivities and intensities. The wavelength λ (lambda) is assigned to the abscissa. Intensities I and spectral sensitivities A are assigned to the ordinate. In accordance with the highly schematic character of the illustration, units are not specified either on the abscissa or on the ordinate. The shapes of the reproduced curves, in particular gradient and profile of flanks, plateaus, shape of maxima, etc., are greatly simplified and with this great simplification do not correspond to reality. The curves merely serve to illustrate the features and properties presented below.

The spectral sensitivity 71 of the S cones of the human eye, the spectral sensitivity 72 of the M cones of the human eye and the spectral sensitivity 73 of the L cones of the human eye have maxima and flanks at different wavelengths, but partly overlap one another. The spectral sensitivities 71, 72, 73 of the S, M and L cones of the human eye define the wavelength range 80 which is visible to the human eye and which extends from approximately 380 nm to 750 nm. The wavelength range in which the sensitivity of the S cones is dominant is designated as the blue wavelength range 81. The wavelength range in which the sensitivity of the M cones is dominant is designated as the green wavelength range 82. The wavelength range in which the sensitivity of the L cones is dominant is designated as the red wavelength range 83. Toward longer wavelengths, the red wavelength range 83 is followed by the infrared wavelength range 84 outside the wavelength range 80 visible to the human eye.

In the development of cameras care is generally taken to ensure that the spectral sensitivities of the camera in the color channels largely correspond to the spectral sensitivities 71, 72, 73 of the S, M and L cones of the human eye. In the case of the camera 30 illustrated above with reference to FIG. 2, the spectral sensitivities in the color channels are determined primarily by the wavelength-dependent reflection properties of the dichroically reflective layers 45, 46 and by spectral sensitivities of the image sensors 51, 52, 53. ToF sensors typically have a spectral sensitivity that extends far into the infrared wavelength range 84.

It is assumed hereinafter that even at long wavelengths the imaging device 32, the prism 40 and the anamorphic lens 48 are transparent and the second dichroically reflective layer 46 is reflective. In this case, the spectral sensitivity 74 of the color channel assigned to the ToF image sensor 53 corresponds to the spectral sensitivity 74 of the ToF image sensor 53. For the blue color channel (image sensor 51) and the green color channel (image sensor 52) it is assumed hereinafter as a simplification that the spectral sensitivities correspond to the spectral sensitivities 71, 72 of the S and M cones, respectively, of the human eye.

FIG. 3 furthermore indicates an emission spectrum 91 of the first light source 21 (cf. FIG. 1) and an emission spectrum 92 of the second light source 22. The emission spectrum 91 of the first light source 21 substantially comprises the blue and the green wavelength range 81, 82. The emission spectrum 92 of the second light source 22 substantially comprises the red wavelength range 83. Alternatively, the second light source 22 can generate an alternative emission spectrum 93 comprising part of the infrared wavelength range 84.

Figure 4:
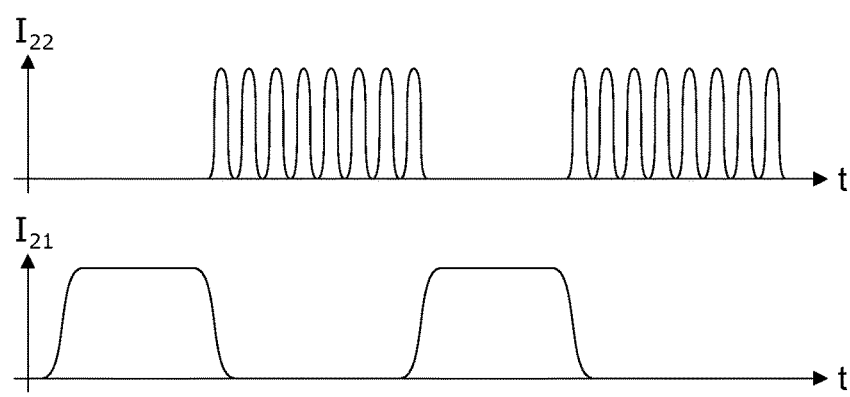
FIG. 4 shows a schematic illustration of a temporal modulation of illumination light.

FIG. 4 shows a schematic illustration of the time-dependent modulation of the illumination light generated by the light source device 20 (cf. FIG. 1). Two schematic diagrams one above the other illustrate at the bottom the temporal modulation of the emission of the first light source 21 and at the top the temporal modulation of the emission of the second light source 22. Time t is in each case assigned to the abscissa and the intensity $I_{21}$ of the illumination light generated by the first light source 21 and coupled into the optical-fiber cable 15 and the intensity $I_{22}$ of the intensity of the illumination light generated by the second light source 22 and coupled into the optical-fiber cable 15 are respectively assigned to the ordinate.

Illumination light is generated alternately by the first light source 21 and the second light source 22. In time intervals in which illumination light is generated by the first light source 21, the intensity $I_{21}$ of the illumination light generated by the first light source 21 is substantially constant. In time intervals in which the second light source 22 generates illumination light, the intensity $I_{22}$ of the illumination light generated by the second light source 22 is temporally high-frequency modulated. The modulation frequency is in particular in the range of a few MHz to a few GHz.

The time intervals in which the first light source 21 generates illumination light and the time intervals in which the second light source 22 generates illumination light alternate in particular with the image repetition frequency, which is typically between 25 Hz and 100 Hz.

Figure 5:
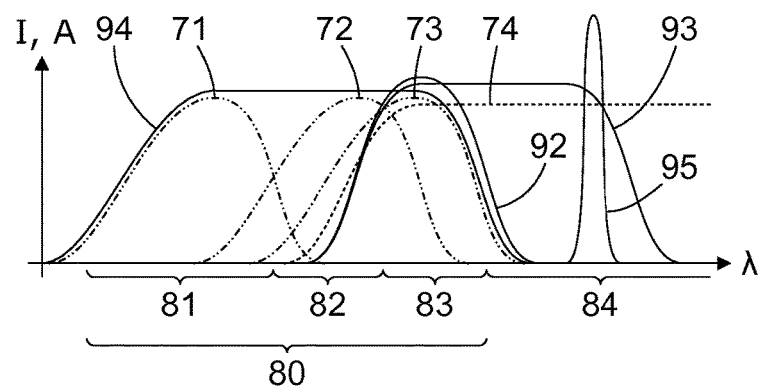
FIG. 5 shows a schematic illustration of wavelength ranges, intensities and spectral sensitivities.

FIG. 5 shows a further schematic illustration of wavelength ranges, spectral sensitivities and intensities. The manner of the illustration corresponds to the illustration in FIG. 3.

The wavelength ranges 80, 81, 82, 83, 84 and the spectral sensitivities 71, 72, 73, 74 of the cones of the human eye and of the color channel assigned to the ToF image sensor correspond to those illustrated above with reference to FIG. 3. The alternative emission spectrum 93 of the second light source 22, said spectrum already being illustrated in FIG. 3, is furthermore illustrated. FIG. 5 furthermore illustrates an alternative emission spectrum 94 of the first light source 21 (cf. FIG. 1) and a further alternative emission spectrum 95 of the second light source 22. The alternative emission spectrum 95 of the second light source 22 is narrowband and corresponds, for example, to the emission spectrum of a semiconductor laser or a narrowband emitting semiconductor diode.

The alternative emission spectrum 94 of the first light source 21 also comprises the red wavelength range 83 besides the blue wavelength range 81 and the green wavelength range 82. In the case of use of a first light source 21 having the alternative emission spectrum 94, the ToF sensor 53, in the time intervals in which the first light source 21 emits the alternative emission spectrum 94, can be used like a simple image sensor for acquiring an intensity image signal for the red wavelength range 83. In the time intervals in which the second light source 22 generates the emission spectrum 92, the alternative emission spectrum 93 or the alternative emission spectrum 95, a distance image signal can be obtained by means of the ToF image sensor 53.

If the first light source 21 generates the emission spectrum 91 illustrated above with reference to FIG. 3, said emission spectrum comprising no or only little red light, in the time intervals in which the second light source 22 generates the emission spectrum 92 or the alternative emission spectrum 93, besides the distance image signal an intensity image signal related to the red color channel can be obtained by means of the ToF image sensor 53.

If the first light source 21 generates red light in an appreciable quantity, for example in the form of the alternative emission spectrum 94 from FIG. 5, and the second light source 22 does so as well, the ToF image sensor 53 can generate a first intensity image signal in the time intervals in which the first light source 21 generates illumination light and a second intensity image signal in the time intervals in which only the second light source 22 generates illumination light. Both intensity image signals generated by means of the ToF image sensor 53 can be used for improving the color rendering in the red color channel on account of the spectra of the two light sources 21, 22, which spectra differ also in the red and infrared wavelength range 83, 84. In particular, a linear combination or a weighted sum or difference of both intensity image signals generated by means of the ToF image sensor 53 is used to obtain an improved intensity image signal.

In so far as the overlap between the spectral sensitivity 74 of the ToF image sensor 53 and the emission spectrum (in particular the emission spectrum 91 shown in FIG. 3) of the first light source 21 is small, the first light source 21 can be operated continuously, in a departure from the illustration in FIG. 4. A larger overlap between the emission spectrum 91 of the first light source 21 and the spectral sensitivity 74 of the ToF image sensor 53 impairs the signal-to-noise ratio in the distance image signal obtained by means of the ToF image sensor 53.

Figure 6:
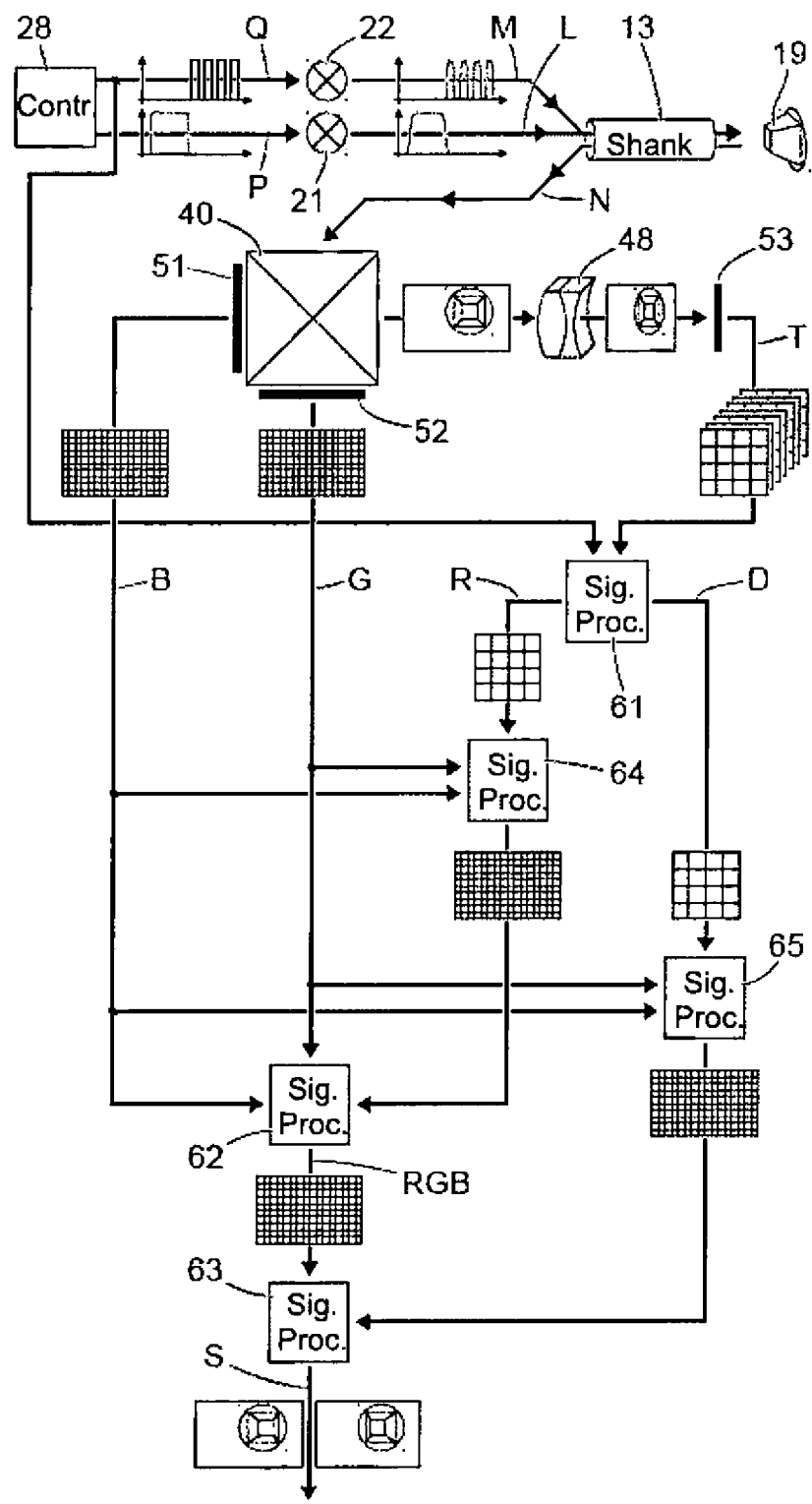
FIG. 6 shows a schematic illustration of a signal processing.

FIG. 6 shows a schematic illustration of a signal processing by means of the light source device 20, the endoscope 10 and the camera 30 from FIGS. 1 and 2. In so far as elements, features and properties of the light source device, of the endoscope and of the camera are illustrated in FIG. 6, this serves merely to illustrate the signal paths. The spatial arrangement in FIG. 6 is not associated with the spatial arrangement in FIGS. 1 and 2 nor with a real spatial arrangement.

The controller 28 of the light source device 20 generates a control signal P for the first light source 21 and a control signal Q for the second light source 22. The first light source 21 generates illumination light L in accordance with the first control signal P, which illumination light L is temporally modulated in particular as in FIG. 4 and has for example the emission spectrum 91 from FIG. 3 or the emission spectrum 94 from FIG. 5. The second light source 22 generates illumination light M in accordance with the second control signal Q, which illumination light is temporally high-frequency modulated in particular as illustrated above in FIG. 4 and has for example one of the emission spectra 92, 93, 95 illustrated in FIGS. 3 and 5.

Both the illumination light L generated by the first light source 21 and the illumination light M generated by the second light source 22 are transmitted by means of the optical-fiber cable 15 (cf. FIG. 1) to the proximal end 11 of the endoscope 10 and transmitted for example by means of one or more optical fibers in the shank 13 to the distal end 12 of the endoscope. For the illumination light L of the first light source 21 and for the illumination light M of the second light source 22, separate optical waveguides can be provided in the optical-fiber cable 15 and in the shank 13 of the endoscope 10. Alternatively, both the illumination light L generated by the first light source 21 and the illumination light M generated by the second light source 22 are transmitted by means of the same optical waveguide or by means of the same optical waveguides.

At the distal end 12 of the endoscope 10 (cf. FIG. 1), the illumination light L, M emerges and is incident on the object 19 to be observed. The illumination light L, M is reflected or returned from the object 19. A part N of the light reflected or returned from the object 19 enters into the shank 13 of the endoscope 10 at the distal end 12 and is transmitted for example by means of a series of rod lens elements or by means of an ordered bundle of optical waveguides to the eyepiece 16 of the endoscope 10 and further to the prism 40 of the camera 30 (cf. FIG. 2).

Portions of the light N which lie in the blue wavelength range 81 (cf. FIG. 3) pass to the image sensor 51 assigned to the blue wavelength range 81 and generate there an image of the object 19 in blue light. The image sensor 51 assigned to the blue wavelength range 81 generates an intensity image signal B assigned to the blue wavelength range 81 or a sensor signal comprising the intensity image signal B.

Portions of the light N which lie in the green wavelength range 82 (cf. FIG. 3) pass to the image sensor 52 assigned to the green wavelength range 82 and generate there an image of the object 19 in green light. The image sensor 52 assigned to the green wavelength range 82 generates an intensity image signal G assigned to the green wavelength range 82 or a sensor signal comprising the intensity image signal G.

Portions of the light N from the object 19 which lie in the red wavelength range 83 and/or in the infrared wavelength range 84 pass via an anamorphic lens 48 to the ToF image sensor 53 and generate there an image of the object 19 in red and/or infrared light. Images of the object 19 having different dimensions are in each case indicated between the prism 40 and the anamorphic lens 48 and between the anamorphic lens 48 and the ToF image sensor 53. The different dimensions of these two images schematically indicate the effect of the anamorphic lens 48 and the matching of the dimensions of the image to the dimensions of the ToF image sensor 53.

The ToF image sensor 53 generates a sensor signal T containing information both about intensities or brightnesses in the red wavelength range and about distances.

In the signal paths of the intensity image signal B related to the blue wavelength range, of the intensity image signal G related to the green wavelength range and of the sensor signal T, different formats of the intensity image signals B, G and of the sensor signal T are indicated by means of checkered rectangles. In accordance with the significantly lower resolution or number of pixels of the ToF image sensor 53 that is taken as a basis here, the sensor signal T is related to a significantly smaller number of columns and lines of pixels than the intensity image signals B, G. By way of example, the image sensors 51, 52 assigned to the blue and to the green color channel in each case generate image signals which reproduce images with a resolution of 1920× 1080 or 1920×1200 pixels (full-HD). In accordance with the resolution of the ToF image sensor 53, the sensor signal T is related for example to approximately 200×200 pixels.

A plurality of planes are indicated in the symbolic illustration of the sensor signal T in FIG. 6. This corresponds to the fact that the sensor signal T contains, besides the two-dimensionality of the intensity image contained or represented, information about a third dimension, namely distances between imaged surface elements and the ToF image sensor 53 or the distal end 12 of the endoscope 10.

The sensor signal T of the ToF image sensor 53 passes to the first signal processing device 61. The first signal processing device 61 furthermore receives the control signal Q for the second light source 22 or a corresponding signal containing information about the phase of the control signal and of the illumination light M generated by the second light source 22. Using the sensor signal T of the ToF image sensor 53 and the control signal Q of the controller 28, the first signal processing device 61 generates an intensity image signal R and a distance image signal D. The intensity image signal R is related to the red wavelength range 83 and/or to the infrared wavelength range 84.

In particular, the intensity image signal R is related only to the red wavelength range 83. In the case of the emission spectrum 94 (cf. FIG. 5) of the first light source 21, the intensity image signal R is generated in particular exclusively on the basis of photons which are incident on the ToF image sensor 53 during the time interval in which the first light source 21 emits illumination light L. Alternatively (in particular in the case of the emission spectrum 91 of the first light source 21 as illustrated in FIG. 3) or additionally, the intensity image signal R or a further intensity image signal can be generated on the basis of photons generated in the ToF image sensor 53 during the time intervals in which the second light source 22 emits light.

The intensity image signal R contains—apart from a brightness which decreases on account of decreasing illuminance with increasing distance—no information about the distance between the object 19 and the ToF image sensor 53 (along the optical path) or about the distance between the object 19 and the distal end 12 of the endoscope 10. The information about distances is contained only in the distance image signal D.

The first signal processing device 61 generates the intensity image signal R and the distance image signal D with the resolution of the ToF image sensor 53 and of the sensor signal T. The resolution of the intensity image signal R is increased by the fourth signal processing device 64 and matched to the resolution of the intensity image signals B, G with respect to the blue and green wavelength ranges. The second signal processing device 62 generates a color image signal RGB using the intensity image signals B, G with respect to the blue and with respect to the green wavelength range and the resolution-matched intensity image signal R with respect to the red wavelength range.

The fifth signal processing device 65 increases the resolution of the distance image signal D and matches it to the resolution of the intensity image signals B, G and of the color image signal RGB. The third signal processing device 63 generates a stereoscopic image signal S using the color image signal RGB and the resolution-matched distance image signal D, said stereoscopic image signal containing or reproducing two images, one for each eye of an observer.

In the case of the embodiment of the camera 30 as described here, the signal path from the ToF image sensor 53 to the second signal processing device 62 or the use of the intensity image signal R generated from the sensor signal T of the ToF image sensor 53 for the generation of a color image signal RGB can constitute a particularly advantageous aspect. In particular, said signal path, compared with many other conventional approaches, makes it possible to use just three image sensors 51, 52, 53. In particular, for producing the camera 30 it is possible to use a conventional beam splitter or a conventional prism 40 with three image sensors 51, 52, 53 assigned to the blue, green and red color channels. Proceeding from this conventional beam splitter, an image sensor 59 (cf. FIG. 2)—in particular the image sensor assigned to the red color channel—is removed and replaced by a ToF image sensor.

Figure 7:
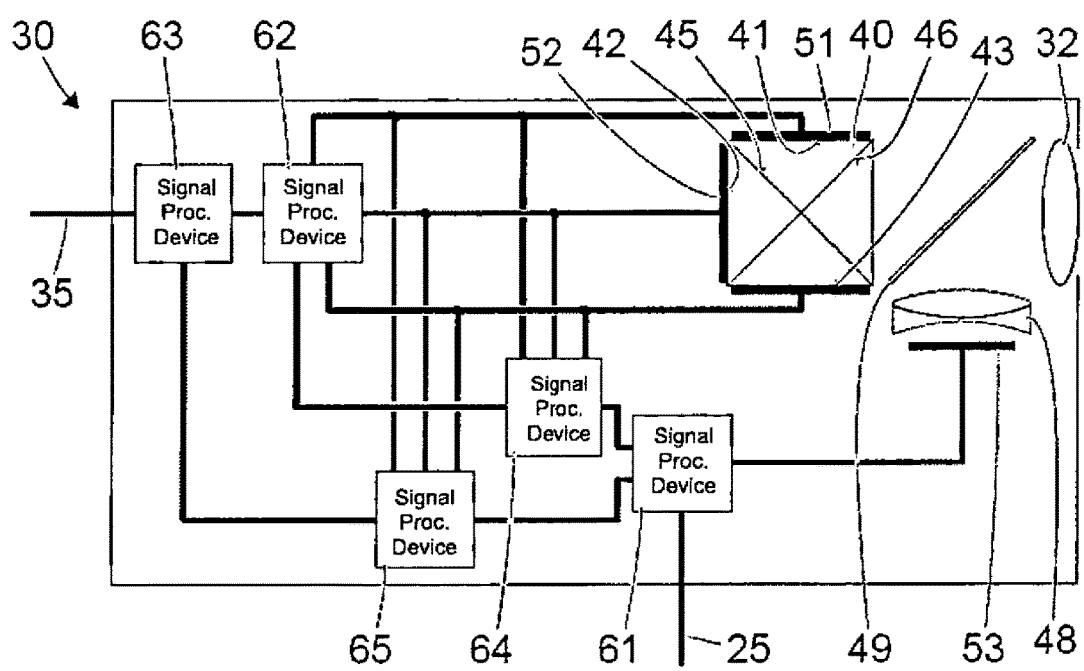
FIG. 7 shows a schematic illustration of a further camera device.

FIG. 7 shows a schematic illustration of a further embodiment of a camera 30, which in some features and properties is similar to the camera illustrated above with reference to FIGS. 1 to 6. Only features, properties and functions of the camera 30 in terms of which the latter differs from the camera illustrated above with reference to FIGS. 1 to 6 are described below.

The camera 30 illustrated in FIG. 7 differs from the camera illustrated above with reference to FIGS. 1 to 6 in particular in that a total of four image sensors are provided. Disposed upstream of a beam splitter in the form of a prism 40 similar to the prism of the camera illustrated above with reference to FIGS. 1 to 6 there is a further beam splitter 49 in the form of a partly transmissive mirror arranged between the imaging device 32 and the prism 40. Three image sensors 51, 52, 54 are arranged at the prism 40, said image sensors being assigned to the blue wavelength range 81, to the green wavelength range 82 and to the red wavelength range 83, respectively. The further beam splitter 49 is provided and designed to direct light in the infrared wavelength range 84 and optionally light of part of the red wavelength range 83 via an anamorphic lens 48 onto a ToF image sensor 53.

The first signal processing device 61 is designed to generate an intensity image signal and a distance image signal in a manner similar to that in the case of the camera illustrated above with reference to FIGS. 1 to 6 using the sensor signal T of the ToF image sensor 53 and the control signal Q for the second light source 22 (cf. FIG. 6). The second signal processing device 62 is designed to generate a color image signal using the intensity image signals generated by the image sensors 51, 52, 54 arranged at the prism 40 and the intensity image signal generated by the first signal processing device 61. By using the intensity image signal originating from the ToF image sensor 53 for generating the color image signal, it is possible to achieve an improvement in the color rendering in particular in the red color channel. In particular, a linear combination or a weighted sum or difference of the intensity image signal generated by means of the ToF image sensor 53 and of the by means of the image sensor 54 assigned to the red wavelength range 83 can be used in order to obtain an improved intensity image signal for the red color channel.

Figure 8:
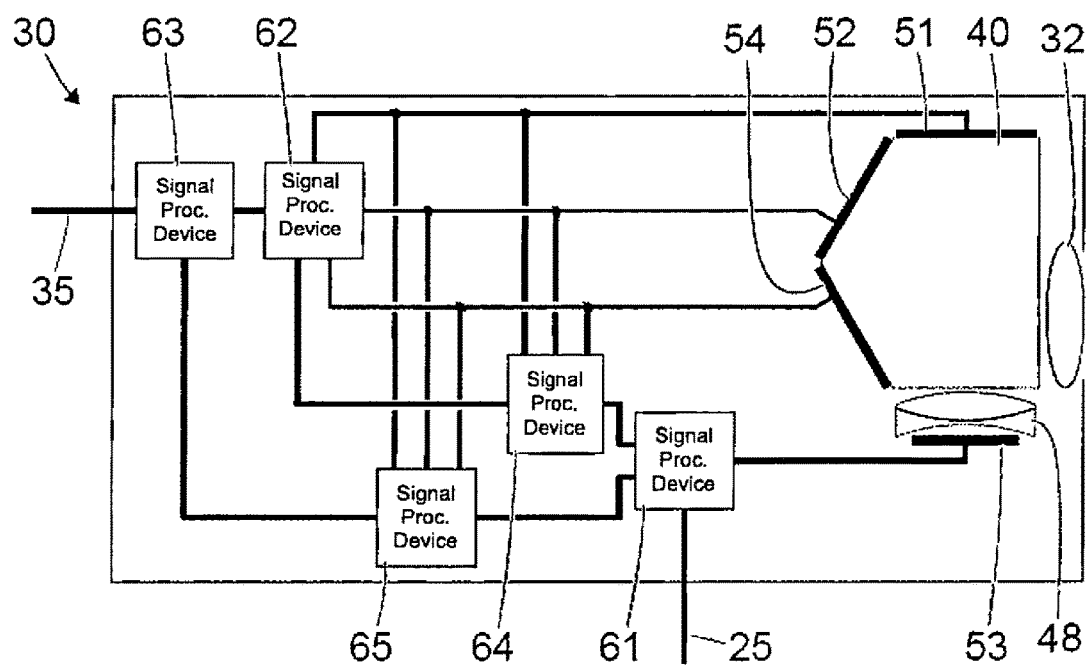
FIG. 8 shows a schematic illustration of a further camera device.

FIG. 8 shows a schematic illustration of a further camera, which in some features, properties and functions is similar to the cameras illustrated above with reference to FIGS. 1 to 7. Only features, properties and functions in terms of which the camera 30 differs from the cameras illustrated above with reference to FIGS. 1 to 7 are illustrated below.

The camera 30 illustrated in FIG. 8 differs from the camera illustrated above with reference to FIG. 7 in particular in that, instead of a prism and a further beam splitter, a prism 40 having four light exit surfaces is provided as a beam splitter. Dichroically reflective layers in the prism 40 are not illustrated in FIG. 8, for the sake of simplicity.

Both the arrangement of two beam splitters in series as illustrated with reference to FIG. 7 and the use of a beam splitter having four (or more) light exit surfaces as illustrated with reference to FIG. 8 and the use of a corresponding number of image sensors increase the mass and the structural volume. The increase in mass of the camera can be compensated for at least in part by lightweight construction, for example by a housing composed of deep-drawn and welded, corrosion-resistant titanium sheet metal.

Instead of a beam splitter with three or more image sensors, in a departure from the illustration with reference to FIGS. 2 to 8, a camera can comprise just a ToF image sensor and a further image sensor. The further image sensor is, for example, a Bayer sensor or some other image sensor having two or more groups of pixels, upstream of which are arranged filters in two (or more) different colors. The further image sensor generates a sensor signal which contains a corresponding number of intensity image signals or can be converted into a corresponding number of intensity image signals.

A linear combination or a weighted sum or difference is formed from the intensity image signal originating from the ToF image sensor and one of the intensity image signals originating from the further image sensor. Furthermore, it is possible to form further linear combinations from the intensity image signal originating from the ToF image sensor and in each case one of the intensity image signals originating from the further image sensor. This linear combination or linear combinations can bring about an improvement in the color rendering and/or simplify for example a differentiation of benign and malignant tissue.

Figure 9:
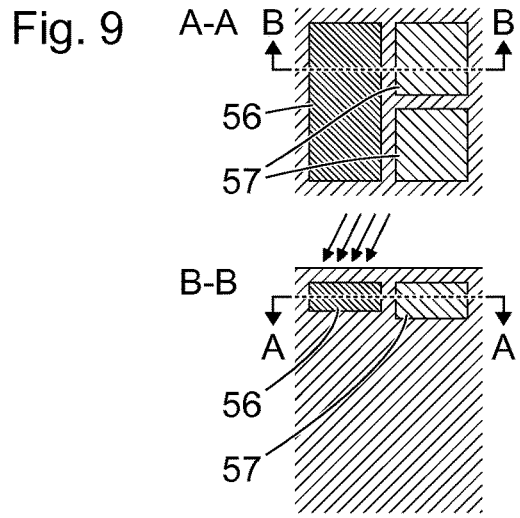
FIG. 9 shows schematic sectional illustrations of a cell of an image sensor.

FIG. 9 shows schematic sectional illustrations of a cell or a pixel of a ToF image sensor. The sectional plane A-A illustrated at the top is parallel to the surface of the ToF image sensor or to the image area into which the image to be acquired is optically imaged. The sectional plane B-B illustrated at the bottom in FIG. 9 is perpendicular to the sectional plane A-A and perpendicular to the image area. The position of the sectional area A-A is illustrated in section along the plane B-B, and the position of the sectional plane B-B is illustrated in section along the plane A-A.

FIG. 9 illustrates one photosensitive element 56 and two storage elements 57 (in particular capacitors). Each pixel contains further components, in particular transistors or other switches and lines, which are not illustrated in FIG. 9 because they take up significantly less structural space. The structural space occupied by the storage elements 57 is typically of an order of magnitude comparable with the structural space of the photosensitive element 56. In conventional ToF image sensors, the photosensitive element 56 and the storage elements 57 are arranged substantially in a plane alongside one another.

In order to increase the resolution of a ToF image sensor, it is necessary to reduce the size of the individual pixel. It is proposed to increase the ratio between the storage capacitance of the storage elements 57 and the area occupied by them in order to reduce their area requirement and thus the area of the individual pixel and to increase the resolution of the ToF image sensor. For this purpose, it is proposed, in particular, to use electrolytic capacitors instead of conventional capacitors having a solid dielectric between the electrodes. Electrolytic capacitors enable a significantly greater capacitance for the same structural space. Conversely, a significantly smaller structural space is required for the same capacitance. The electrolyte can be introduced by printing regularly arranged droplet arrays, vapor deposition or condensing or in some other way. Furthermore, it is proposed to microscopically structure and thus enlarge the areas of the capacitor electrodes by means of porous silicon or other porous semiconductor structures or by means of carbon nanotubes in order to improve the ratio between capacitance and occupied structural space.

Figure 10:
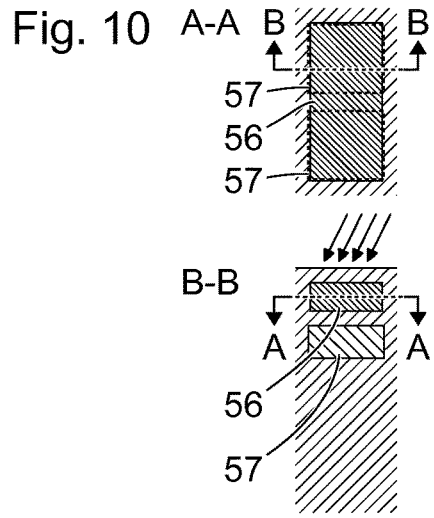
FIG. 10 shows schematic sectional illustrations of a cell of a further image sensor.

FIG. 10 shows schematic sectional illustrations of a further embodiment of a pixel of a ToF image sensor, which is similar in some features and properties to the embodiment in FIG. 9. The manner of the illustration in FIG. 10 corresponds to the manner of the illustration in FIG. 9.

The pixel in FIG. 10 differs from the pixel illustrated above with reference to FIG. 9 in that the storage elements 57 are not arranged alongside, but rather below the photosensitive element 56. As a result, the area occupied by the individual pixel can be drastically reduced, to approximately half in the example illustrated.

Figure 11:
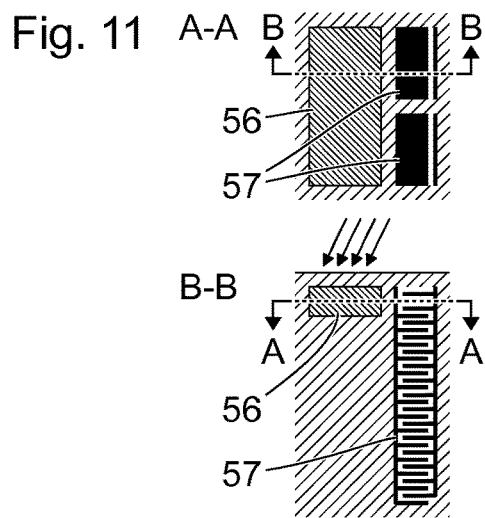
FIG. 11 shows schematic sectional illustrations of a cell of a further image sensor.

FIG. 11 shows schematic sectional illustrations of a further embodiment of a pixel of a ToF image sensor, which is similar in some features and properties to the embodiments in FIGS. 9 and 10. The manner of the illustration in FIG. 11 corresponds to the manner of the illustration in FIGS. 9 and 10.

The embodiment in FIG. 11 differs from the embodiment in FIG. 9 in particular in that the individual storage element 57 comprises a sandwich-like stacking of a plurality or large number of planar capacitor electrodes which extends to a greater depth, said capacitor electrodes being electrically conductively connected alternately to one of two poles. This can make it possible to drastically increase the ratio between the effective capacitor area or the effective areas of the capacitor electrodes, on the one hand, and the basic area—measured parallel to the sectional plane A-A—of the storage elements 57, on the other hand.

Figure 12:
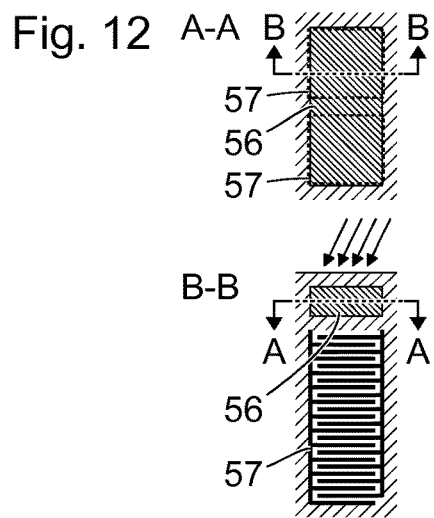
FIG. 12 shows schematic sectional illustrations of a cell of a further image sensor.

FIG. 12 shows schematic sectional illustrations of a further embodiment of a pixel of a ToF image sensor, which is similar in some features and properties to the embodiments in FIGS. 9 to 11. The manner of the illustration in FIG. 12 corresponds to the manner of the illustration in FIGS. 9 to 11.

The embodiment in FIG. 12 differs from the embodiment in FIG. 11 in particular in that the storage elements 57 are not arranged alongside, but rather—in a manner similar to that in the embodiment of FIG. 10—below the photosensitive element 56. This can enable a further drastic reduction of the area occupied by the individual pixel (measured parallel to the sectional plane A-A) and a corresponding improvement in the resolution of the ToF image sensor.

Figure 13:
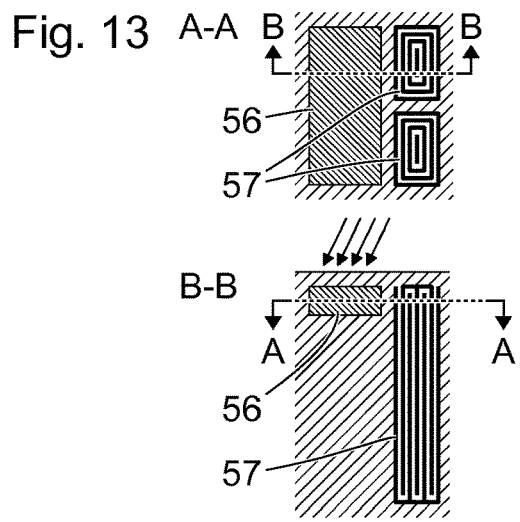
FIG. 13 shows schematic sectional illustrations of a cell of a further image sensor.

FIG. 13 shows schematic sectional illustrations of a further embodiment of a pixel of a ToF image sensor, which is similar in some features and properties to the embodiments in FIGS. 9 to 12. The manner of the illustration in FIG. 13 corresponds to the manner of the illustration in FIGS. 9 to 12.

The embodiment from FIG. 13 differs from the embodiment in FIG. 11 in particular in that vertical capacitor electrodes or capacitor electrodes perpendicular to the sectional plane A-A are provided instead of horizontal capacitor electrodes or capacitor electrodes parallel to the sectional plane A-A. The capacitor electrodes have in particular the form of lateral surfaces of cylindrical or prismatic columns. A plurality of electrode surfaces having different cross sections are arranged one in another, are insulated from one another by dielectric and are electrically conductively connected alternately to the two poles of a storage element. Instead of a rectangular cross section, a storage element 57 can have in each case a circular or elliptical cross section in the plane A-A. Furthermore, the electrodes can be arranged in a double spiral.

Figure 14:
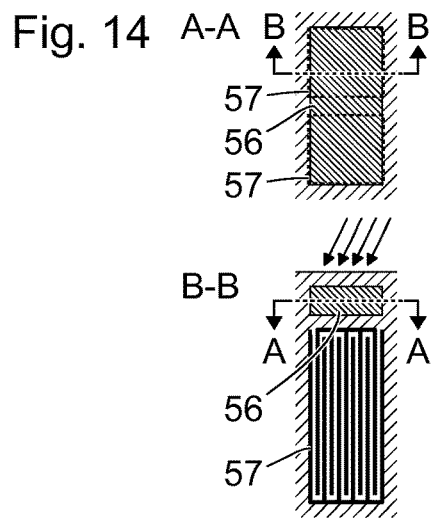
FIG. 14 shows schematic sectional illustrations of a cell of a further image sensor.

FIG. 14 shows schematic sectional illustrations of a further embodiment of a pixel of a ToF image sensor, which is similar in some features and properties to the embodiments in FIGS. 9 to 13. The manner of the illustration in FIG. 14 corresponds to the manner of the illustration in FIGS. 9 to 13.

The embodiment in FIG. 14 differs from the embodiment illustrated above with reference to FIG. 13 in particular in that the storage elements 57 are not arranged alongside, but rather—in a manner similar to that in the embodiments in FIGS. 10 and 12—below the photosensitive element 56.

Figure 15:
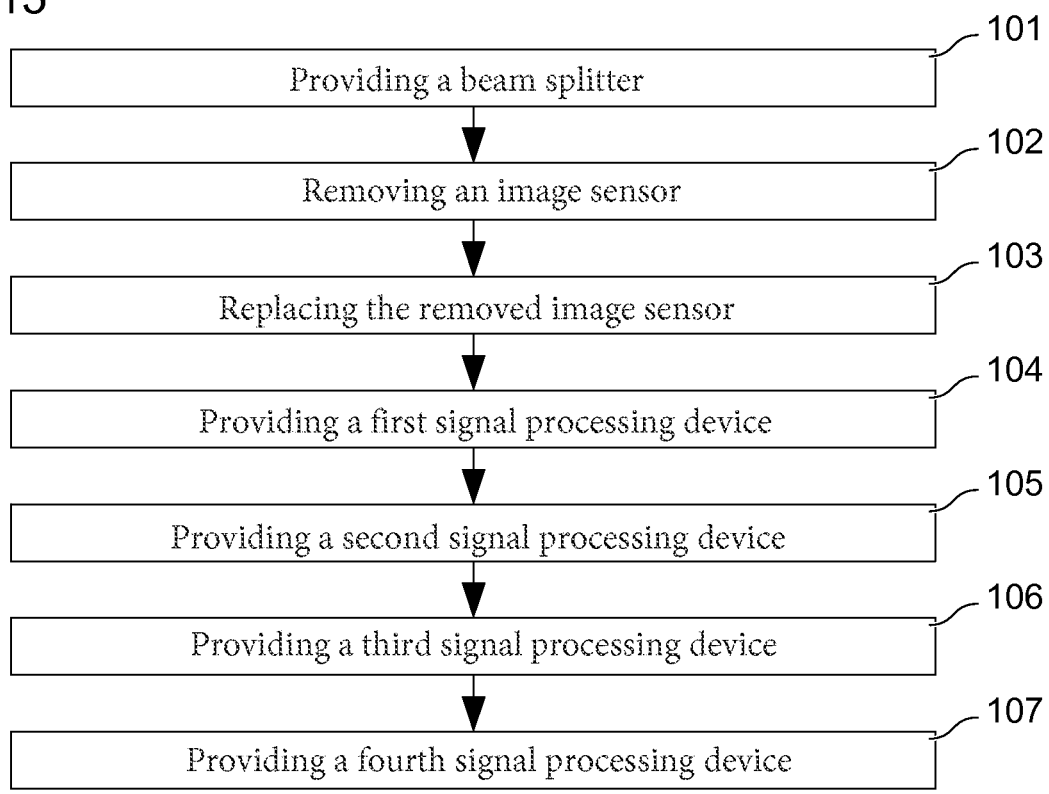
FIG. 15 shows a schematic flowchart of a method for producing a camera device.

FIG. 15 shows a schematic flowchart of a method for producing a camera or a camera device. The method is also suitable for producing a camera or a camera device whose properties and features deviate from those illustrated above with reference to FIGS. 1 to 8. Nevertheless, by way of example, reference signs from FIGS. 1 to 8 are used below in order to simplify the understanding.

A first step 101 involves providing a beam splitter 40 with a plurality of image sensors 51, 52, 59. The beam splitter 40 is, in particular, a prism having a plurality of dichroically reflective layers which have the effect that light is imaged onto different image sensors 51, 52, 59 depending on its wavelength. It is assumed by way of example below that the image sensors 51, 52, 59 at the beam splitter 40 are respectively assigned to one of the color channels blue, green and red.

A second step 102 involves removing an image sensor 59 from the beam splitter 40. It is assumed hereinafter that the removed image sensor 59 was assigned to the red wavelength range or the red color channel.

A third step 103 involves replacing the removed image sensor 59 by an image sensor 53 suitable for the spatially resolved acquisition of distances on the basis of temporally high-frequency modulatable sensitivity. It is assumed hereinafter that the replacing image sensor 53 is a ToF image sensor and has a lower resolution than the image sensors 51, 52 remaining at the beam splitter.

If the replacing image sensor 53 has a different width or height in comparison with the image sensors 51, 52 remaining at the beam splitter 40, the third step 103 of replacing can comprise a step of providing a matching device. If the replacing image sensor 53 has a different ratio between height and width in comparison with the image sensors 51, 52 remaining at the beam splitter 40, the matching device 48 is or comprises an anamorphic lens, in particular.

A fourth step 104 involves providing a first signal processing device and coupling it to the replacing ToF image sensor 53. The first signal processing device 61 provided in the fourth step 104 can be integrated with the replacing ToF image sensor. In this case, the third step 103 and the fourth step 104 coincide. The first signal processing device 61 is designed for receiving a sensor signal from the replacing ToF image sensor 53 and for receiving information about the temporal modulation of illumination light (in particular about the phase of the temporal modulation) and for generating an intensity image signal and a distance image signal.

A fifth step 105 involves providing a second signal processing device 62 and coupling it to the first signal processing device 61 and to the image sensors 51, 52 remaining at the beam splitter 40. The second signal processing device 62 provided in the fifth step 105 is designed to receive intensity image signal B, G which are related to the blue and to the green wavelength range, respectively, from the image sensors 51, 52 remaining at the beam splitter 40 and an intensity image signal related to the red wavelength range from the first signal processing device 61. Furthermore, the second signal processing device 62 is designed to generate a color signal RGB using the intensity image signals.

A sixth step 106 involves providing a third signal processing device 63 and coupling it to the first signal processing device 61 and to the second signal processing device 62. The third signal processing device 63 provided in the sixth step 106 is designed to receive the distance image signal from the first signal processing device 61 and the color image signal from the second signal processing device 62 and to generate a stereoscopic image signal S using the distance image signal D and the color image signal RGB.

An optional seventh step 107 involves matching a fourth signal processing device 64 for matching the resolution of the intensity image signal R generated by the first signal processing device 61 to the resolution of the intensity image signals B, G from the image sensors 51, 52 that remained at the beam splitter 40. The seventh step 107 can be omitted in particular if the resolution of the ToF image sensor 53 provided in the third step 103 corresponds to the resolution of the beam splitters 51, 52 that remained at the beam splitter 40.

FIG. 16 shows a schematic flowchart of a method for acquiring optical properties in a plurality of different wavelength ranges and spatial structure properties of an object. The method can be performed by means of a camera or a camera device having features and properties that deviate from the features and properties illustrated above with reference to FIGS. 1 to 8. Furthermore, the method can be performed with a camera or camera device produced by means of a method having steps, properties and features deviating method illustrated with reference to FIG. 15. Nevertheless, by way of example, reference signs from FIGS. 1 to 8 are used below in order to simplify the understanding.

A first step 111 involves illuminating an object 19 with illumination light generated by a first light source 21. The emission spectrum of the first light source 21 comprises, in particular, the wavelength ranges perceived as blue and green by the human eye and optionally in addition the wavelength range perceived as red by the human eye. A second step 112 involves acquiring a first sensor signal by means of an image sensor assigned to the blue wavelength range. The first sensor signal comprises an intensity image signal assigned to the blue wavelength range or to the blue color channel. A third step 113 involves acquiring a second sensor signal by means of an image sensor 52 assigned to the green wavelength range. The second sensor signal comprises an intensity image signal assigned to the green wavelength range. The second step 112 and the third step 113 are performed in particular at the same time as the first step 111.

A fourth step 114 involves illuminating the object 19 by means of temporally high-frequency modulated illumination light generated by a second light source 22. The second light source generates, in particular, an emission spectrum in the red and/or infrared wavelength range.

A fifth step 105 involves acquiring a third sensor signal of an image sensor 53 assigned to the red and/or infrared wavelength range. The third sensor signal contains both information about the temporally averaged intensity of the illumination light reflected or returned from the object 19 (and, if appropriate, furthermore of the light emitted by the object 19) and information about distances between the object 19 or the surface regions thereof and the image sensor, the camera or a distal end 12 of an endoscope 10.

A sixth step 116 involves generating an intensity image signal R related to the red and/or to the infrared wavelength range using the third sensor signal T. A seventh step 117 involves generating a distance image signal D using the third sensor signal and information about the modulation, in particular the phase of the modulation, of the illumination light. The sixth step 116 and the seventh step 117 are performed in particular directly after the fifth step 115 by a first signal processing device 61.

An eighth step 118 involves matching the resolution of the first sensor signal acquired in the second step, of the second sensor signal acquired in the third step and of the intensity image signal generated in the sixth step to one another. In particular, the lower resolution of the intensity image signal R generated in the sixth step is matched to the higher resolution of the intensity image signals B, G contained in the first sensor signal and the second sensor signal. The eighth step 118 contains in particular a ninth step of interpolating the intensity image signal generated in the sixth step 116 for positions of pixels of the images described by the other two intensity image signals B, G.

A tenth step 120 involves generating a color image signal RGB using the intensity image signals B, G, R. The tenth step 120 is performed in particular by a second signal processing device 62.

An eleventh step 121 involves generating a stereoscopic image signal S using the color image signal RGB and the distance image signal D. The eleventh step 121 is performed in particular by a third signal processing device 63.

An optional twelfth step 122 involves controlling the representation of a stereoscopic image by means of the stereoscopic image signal S. The twelfth step 122 is performed in particular by a screen 39 or with the aid of a screen 39.

All the steps illustrated can be repeated with an image repetition frequency which is in the range of 25 Hz to 100 Hz, for example, in order to give the observer the impression of a continuous movement. The first step 111, the second step 112 and the third step 113, on the one hand, and the fourth step 114, the fifth step 115, the sixth step 116, the seventh step 117 and the eighth step 118, on the other hand, form two method sections or groups of steps which can be performed in an alternating manner or alternately, simultaneously or partly simultaneously. For example in the control of illumination light as illustrated with reference to FIG. 4, the first step 111, the second step 112 and the third step 113 are performed substantially within the time interval within which the first light source 21 (cf. FIGS. 1 and 6) emits illumination light. The fourth step 114, the fifth step 115, the sixth step 116, the seventh step 117 and the eighth step 118 are performed within the time interval within which the second light source 22 emits temporally high-frequency modulated illumination light.

The invention claimed is:

1. A camera device for acquiring optical properties in a plurality of different wavelength ranges and spatial structure properties of an object, comprising:
    a beam splitter for splitting light coming from the object into the plurality of different wavelength ranges;
    a first image sensor for generating a first sensor signal related to a first predetermined wavelength range, wherein the first image sensor is designed for acquiring an intensity of the first predetermined wavelength range and, on the basis of a temporally modulatable sensitivity, is designed for acquiring a distance between the object and the camera device from a time of flight of light;
    a first signal processing device for generating a first intensity image signal and a distance image signal using information about the temporal modulation of illumination light and the first sensor signal, wherein the distance image signal represents the spatial structure properties of the object;
    at least one second image sensor for generating a second sensor signal, which comprises a second intensity image signal for a second predetermined wavelength range;
    a second signal processing device for generating a color image signal from the first intensity image signal and the second intensity image signal, wherein the color image signal represents the optical properties of the object;
    wherein the first predetermined wavelength range consists of a red wavelength range and the second predetermined wavelength range comprises a blue wavelength range.

2. The camera device according to claim 1, wherein the first wavelength range lies at least partly within the wavelength range visible to the human eye.

3. The camera device according to claim 1, wherein the second signal processing device is designed to generate the color image signal without using the distance image signal.

4. The camera device according to claim 1, wherein the first image sensor and the second image sensor have different resolutions, furthermore comprising:
    a signal processing device for matching a first resolution of the first intensity image signal and a second resolution of the second intensity image signal to one another.

5. The camera device according to claim 4, wherein a further signal processing device is designed to interpolate, for the purpose of matching different resolutions, the intensity image signal having the lower resolution for positions of pixels of the intensity image signal having the higher resolution.

6. The camera device according to claim 5, wherein the further signal processing device is designed to use, for the purpose of interpolation, information from the intensity image signal having the higher resolution.

7. An endoscope or exoscope comprising a camera device according to claim 1.

8. The device of claim 1 wherein the first signal processing device is completely integrated into the first image sensor.

9. The device of claim 1 wherein the first image intensity signal comprises an intensity value for the first predetermined wavelength range for each pixel of a first image of the object, and the first distance signal comprises a distance value for each pixel of the first image.

10. The device of claim 1 wherein at least a portion of the first predetermined wavelength range does not overlap with the second predetermined wavelength range, and at least a portion of the second predetermined wavelength range does not overlap with the first predetermined wavelength range.

11. A method for acquiring optical properties in a plurality of different wavelength ranges and spatial structure properties of an object, comprising the following steps:
    illuminating the object with illumination light that is temporally modulated in a predetermined manner;
    acquiring a first sensor signal, which is related to a first predetermined wavelength range, by means of a first image sensor having temporally modulated sensitivity and intensity sensitivity of the first predetermined wavelength range;
    generating a first intensity image signal using the first sensor signal;
    generating a distance image signal using information about the temporal modulation of the illumination light and the first sensor signal;
    acquiring a second intensity image signal, which is related to a second predetermined wavelength range, by means of a second image sensor;
    generating a color image signal using the first intensity image signal and the second intensity image signal,
    wherein the color image signal represents the optical properties of the object and the distance image signal represents the spatial structure properties of the object; and
    the first predetermined wavelength range consists of a red wavelength range and the second predetermined wavelength range comprises a blue wavelength range.

12. The method according to claim 11, wherein the color image signal is generated without using the distance image signal.

13. The method according to claim 11, wherein the resolutions of the first intensity image signal and of the second intensity image signal differ from one another, furthermore comprising the following step:
    matching the resolutions to one another.

14. The method according to claim 13, wherein matching the resolutions comprises interpolating the intensity image signal having the lower resolution for positions of pixels of the image signal having the higher resolution using information from the image signal having the higher resolution.

15. A camera device for acquiring optical properties of an object, comprising:
    a first image sensor generating a sensor signal related to a first wavelength range, acquiring an intensity of the first wavelength range and, on the basis of a temporally modulatable sensitivity, acquiring a distance between the object and the camera device from a time of flight of light;
    a first signal processing device for generating a first intensity image signal and a distance image signal using information about the temporal modulation of illumination light and the first sensor signal;
    a second image sensor generating a second sensor signal having a second intensity image signal for a second wavelength range;
    a second signal processing device generating a color image signal from the first intensity image signal and the second intensity image signal;
    wherein the first wavelength range consists of a red wavelength range and the second wavelength range comprises a blue wavelength range.

16. The device of claim 15 further comprising a beam splitter splitting light coming from the object into the first wavelength range, the second wavelength range, and a third wavelength range.

17. The device of claim 16 further comprising a third image sensor generating a third sensor signal having a third intensity image signal for a third wavelength range, wherein the second signal processing device generates a color image signal from the third intensity image signal.

18. The device of claim 17 wherein the first wavelength range comprises a red wavelength range, the second wavelength range comprises a blue wavelength range, and the third wavelength range comprises a green wavelength range.

19. An endoscope or exoscope comprising a camera device according to claim 18.

20. The device of claim 15 wherein the second sensor generates a third sensor signal having a third intensity image signal for a third wavelength range, and the second signal processing device generates a color image signal from the third intensity image signal.

21. The device of claim 20 wherein the second sensor comprises a Bayer sensor.

* * * * *